(12) United States Patent
Parkin et al.

(10) Patent No.: US 8,475,386 B2
(45) Date of Patent: Jul. 2, 2013

(54) SYSTEMS, METHODS AND DEVICES FOR MAINTENANCE, GUIDANCE AND/OR CONTROL

(75) Inventors: William G. Parkin, Brighton (AU); Mark S. Leaning, Castle Bytham (GB)

(73) Assignee: Applied Physiology Pty. Ltd., Crows Nest, New South Wales (AU)

( * ) Notice: Subject to any disclaimer, the term of this patent is extended or adjusted under 35 U.S.C. 154(b) by 370 days.

(21) Appl. No.: 12/735,597

(22) PCT Filed: Jan. 30, 2009

(86) PCT No.: PCT/AU2009/000087
§ 371 (c)(1),
(2), (4) Date: Dec. 23, 2010

(87) PCT Pub. No.: WO2009/094700
PCT Pub. Date: Aug. 6, 2009

(65) Prior Publication Data
US 2011/0087116 A1    Apr. 14, 2011

Related U.S. Application Data

(60) Provisional application No. 61/006,790, filed on Jan. 31, 2008, provisional application No. 61/006,895, filed on Feb. 5, 2008.

(51) Int. Cl.
*A61B 5/02*    (2006.01)
(52) U.S. Cl.
USPC .............................. 600/485; 600/504; 600/483

(58) Field of Classification Search
USPC .................................. 600/481, 485, 483, 504
See application file for complete search history.

(56) References Cited

U.S. PATENT DOCUMENTS

| 4,993,420 A | 2/1991 | Welkowitz et al. |
| 5,217,019 A | 6/1993 | Hughes |

FOREIGN PATENT DOCUMENTS

WO    WO97/31568 A1    9/1997

OTHER PUBLICATIONS

International Search Report for PCT/AU2009/000087 dated Mar. 19, 2009.

*Primary Examiner* — Navin Natnithithadha
*Assistant Examiner* — Etsub Berhanu
(74) *Attorney, Agent, or Firm* — Jones Day

(57) ABSTRACT

Methods, systems, devices and computer program products for providing maintenance, guidance and/or control of certain systems are disclosed. Typically, in some aspects the systems are complex. Also disclosed are methods, systems, devices and computer program products for providing therapeutic guidance for controlling a subject's circulation. One such method comprises the steps of: (i) determining the subject's present and desired circulatory states as a function of at least mean systemic filling pressure (Pms), heart efficiency (EH) and systemic vascular resistance (SVR); (ii) determining a target direction of a trajectory from the subject's present circulatory state to said subject's desired circulatory state, wherein treatment of the subject so as to traverse the trajectory will cause the subject's circulatory state to move towards a desired circulatory state; and (iii) visually representing the target direction of the trajectory.

17 Claims, 24 Drawing Sheets

VARIANT OF STANDALONE CONFIGURATION.
SYSTEM CONNECTED TO SEPARATE CARDIAC OUTPUT MONITOR.

A CONFIGURATION OF THE VISUAL DISPLAY
OF A CIRCULATORY GUIDANCE SYSTEM.

FIG. 33a and 33b
PHYSICAL ARRANGEMENTS OF CIRCULATORY
GUIDANCE SYSTEMS WITH STANDARD BEDSIDE MONITORS
a)
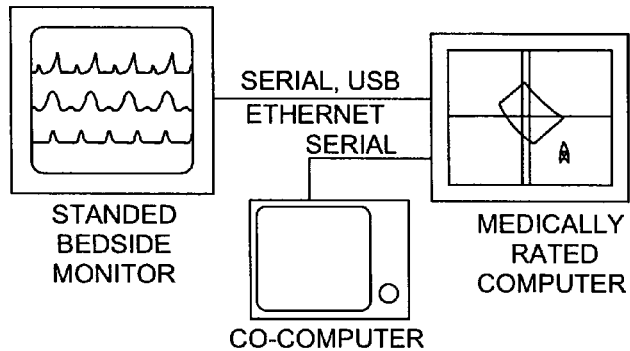
b) 1)
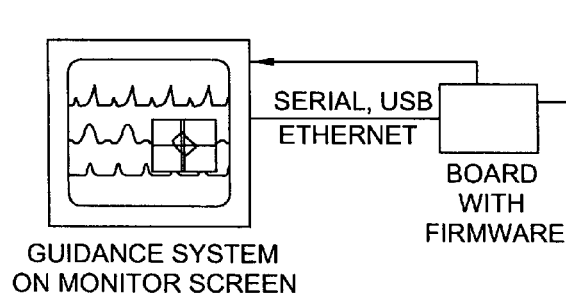
b) 2)
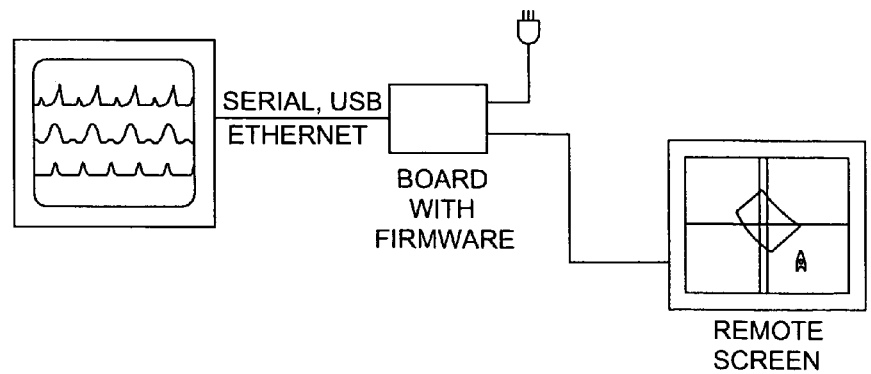

FIG. 33c and 33d
c)
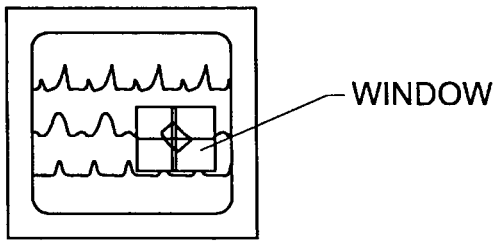
STANDARD MONITOR
GUIDANCE SOFTWARE
RESIDENT IN MONITOR
GUIDANCE INSTRUMENT
IN WINDOW ON MONITOR
d)
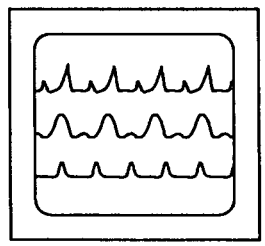
STANDARD MONITOR
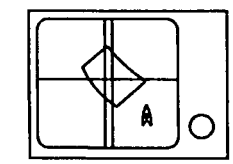
CO MONITOR
GUIDANCE SOFTWARE INSIDE
GUIDANCE SYSTEM
DISPLAYED ON
SUBSIDIARY MONITOR
SCREEN

I.V. SYSTEMS ARE A SUBSET OF
CIRCULATION CONTROL SYSTEMS

BLOOD PRESSURE CONTROL SYSTEMS

DIALYSIS MACHINE - VOLUME CONTROL

SYSTEMS, METHODS AND DEVICES FOR MAINTENANCE, GUIDANCE AND/OR CONTROL

CROSS-REFERENCE TO RELATED APPLICATIONS

This application is the U.S. National Phase application of International Application No. PCT/AU2009/000087, filed 30 Jan. 2009, which designates the United States and was published in English, and which claims priority from U.S. Provisional Application filed on Jan. 31, 2008, Ser. No. 61/006,790, entitled "SYSTEMS, METHODS, AND DEVICES, FOR MAINTENANCE, GUIDANCE AND CONTROL" and U.S. Provisional Application filed on Feb. 5, 2008, Ser. No. 61/006,895, entitled "SYSTEMS, METHODS, AND DEVICES, FOR MAINTENANCE, GUIDANCE AND CONTROL". Each of these related applications, in their entirety, are hereby incorporated by reference.

FIELD OF THE DISCLOSURE

This disclosure relates to systems, methods and devices for maintenance, guidance and/or control of certain systems. In certain aspects, this disclosure relates to systems, methods and devices for therapeutic maintenance, guidance and/or control of mammalian circulation using measurement, interpretation, and/or therapy.

BACKGROUND

External monitoring and control of the certain complex systems is an important yet complex and difficult problem in many situations. For example, external monitoring and control of the circulation is an important yet complex and difficult problem in humans and other mammals, particularly in acutely disordered and severely diseased states. It is one of the most commonly performed tasks in human and veterinary intensive care units and other areas of critical care including anesthesia and emergency care. The task involves the measurement of variables relating to the circulation including blood pressures, blood flows (cardiac output), heart rate, and oxygen levels. In current clinical practice, a physician (or veterinarian) or nurse interprets the measured data and applies various diagnostic and therapeutic interventions. Typical therapies include infusion of volume (e.g., in the form of normal saline), diuretics, vasoconstrictors and vasodilators, and medications that affect the strength, rhythm or relaxation of the heart. One of the aims of this clinical task is to maintain the circulatory state at a desired level. This desired level is usually articulated in the patient record, but not always consistently. The purpose of the desired state is to ensure adequate blood and oxygen perfusion to vital tissues and removal of metabolic products.

Current circulatory management relies primarily on the education, training and experience of the bedside clinician team, which in practice has produced high variability in approaches and results. A common concept is that of pre-load. One definition of pre-load in cardiac physiology is the pressure stretching the ventricle of the heart, after passive filling and atrial contraction. If the chamber is not mentioned, it is usually assumed to be the left ventricle. For example, if the pre-load is low, then an increase of circulating blood volume may be indicated (by increased administration of normal saline or volume expander). Unfortunately, pre-load is a qualitative concept and not a quantitative measure and there are numerous different definitions of pre-load.

Some intensive care units are beginning to introduce paper protocols for circulatory management. However, the most common practice is that of individual interpretation of the varying monitored data and judgment on therapy change.

A number of problems arise from current practice. A wide variety of circumstances including acute subject problems, complexity, clinical inexperience, lack of vigilance and confusion over the desired state can result in the circulation entering areas compromising a subject's wellbeing. This may require extra clinical effort, medications and time to return the circulation to a more desirable state. Furthermore, the perturbed state may itself entail side effects, for example, atrial fibrillation in an overpowered circulation and/or shock and organ failure if pressures and flows are insufficient. These side effects increase morbidity, prolong time in intensive care, increase the risk of death and add considerably to the costs of care.

A need therefore exists to provide methods, systems and/or devices for improving guidance and/or control in certain systems such as complex systems. A need also exists to improve the clinical process of improving circulatory guidance and/or control of unstable circulations in warm blooded animals and provide related methods, systems and/or devices. A need also exists to improve the critical care clinical process of monitoring, treating, and/or improving circulatory guidance and/or control of unstable circulations in warm blooded animals and provide related methods, systems and/or devices. A need also exists to provide methods, systems and/or devices for improving circulatory guidance and/or control in subjects, thereby reducing, among other things, the hazard associated with side effects. A need also exists to improve the clinical process of improving circulatory guidance and/or control by systematizing the care of unstable circulations and/or supporting a team approach to such care. The present disclosure provides various combinations of systems, methods, and/or devices for the care, the guidance and/or the control of certain types of systems. Certain embodiments may also produce better end results for the systems.

SUMMARY

Certain embodiments relate to systems, methods and devices for maintenance, guidance and/or control of certain systems for use in critical care. For example, many critically ill and high-risk patients admitted to intensive care, or in other settings, require circulatory intervention or support. In certain embodiments, the delivery of circulatory support often involves selecting at least certain hemodynamic values to target and deciding which interventions should be used to move towards and/or achieve desired endpoints or targets. In certain embodiments, interventions for circulatory state management can be to some extent classified into at least three types: fluid therapy for control, or substantial control, of volume state; therapies to improve heart performance such as inotropes, heart rate and rhythm interventions; and vasoactive therapies (dilators and constrictors). Optimal application of these therapies in critically ill and high-risk patients is surprisingly lacking in the art.

Clinical data to support circulatory intervention to achieve various explicitly stated haemodynamic targets in a number of settings, such as septic shock and high-risk operative patients are known. However, translation of these recommendations into clinical practice is often subjective in practice and presents numerous challenges to the staff providing circulatory intervention. Frequently circulatory control is needed for 24 hours per day and sometimes for weeks or other extended time periods. While specific setting of objective targets may occur the use of different interventions by various staff at various levels of skill to achieve these targets often involves subjective decision making. As disclosed herein, the task of achieving targeted circulatory support in shocked and high-risk patient groups is aided by a computerised point of care guidance systems where guidance is determined at least in part by objective rules that are physiologically based and continually adapt to the patient's state. Certain embodiments disclosed herein provide a computerized circulatory guidance system that is a flexible platform to assist the delivery of circulatory interventions to achieve explicit targets. Certain disclosed embodiments provide systems, methods and devices that acquires haemodynamic data from the bedside monitor and graphically represents physician determined explicit targets in relation to present patient measured variables. In certain embodiments the haemodynamic data is acquired automatically. Both the patient's position and the targets may be displayed visually, for example, on volumetric, resistance and heart performance axes and a guidance arrow continually indicates which next therapy (i.e. volumetric, vasoactive/resistive or cardioactive) will take the patient toward the desired blood pressure, cardiac output and oxygen delivery targets.

Certain embodiments relate to systems, methods, devices and computer program products for providing maintenance, guidance and/or control of certain complex systems.

Certain embodiments relate to systems, methods and devices for therapeutic maintenance, guidance and/or control of mammalian circulation using measurement, interpretation and/or therapy. Certain embodiments relate to computer-assisted methods for therapeutic guidance for controlling a subject's circulation. Exemplary subjects that may be suitable include a range of patients with unstable circulations presenting to the ICU critical care units, operating rooms, anesthesia, high dependency care, emergency rooms, trauma and field medicine, with exemplary conditions including, for example, pre & post open heart surgery, pre & post major surgery, septic shock, renal failure, major burns, major trauma, cardiogenic shock or combinations thereof.

Certain embodiments may also produce better end results for the systems. In some embodiments, better end results may include improved circulatory control in which blood pressure, cardiac output and/or oxygen delivery are controlled, or substantially controlled, to desired values.

For example, circulatory targets could be varied to those more appropriate to the patient, as judged from the system, and these targets acquired faster and more accurately. By providing better care monitoring and/or guidance certain embodiments will produce better end results (or substantially better end results), less side effects (or substantially less side effects), more efficient care guidance (or substantially more efficient care guidance) and/or more efficient treatment (or substantially more efficient treatment) of the patient. Some examples of better clinical end results are increased survival, reduced length of stay and increased functioning following hospital discharge. Using the embodiments disclosed herein the average care giver (or a range care givers with vary levels of skill) is able to acquire the desired circulatory target at least as fast as, or substantial as fast, as an expert physician who is dedicated to the task of monitoring the patient. Using certain embodiments disclosed herein a range of care givers with various levels of experience are able to acquired the desired circulatory target 5%, 10%, 15%, 20%, 25% or 30% faster then the same care givers would achieve without such a monitoring system. In addition, in many situations the guidance given as to how to acquire the desired target will produce better end results (or substantially better end results), less side effects (or substantially less side effects), more efficient care guidance (or substantially more efficient care guidance), and/or more efficient treatment (or substantially more efficient treatment) of the patient. In addition, the disclosed embodiments provide a regular monitoring of the patients state and allow for frequent adjustments to the patient based on how that patients status evolves. Using certain embodiments disclosed it is possible to monitor and assess the circulatory state of a patient at frequent time intervals (for example, every 2, 5, 10, 20, 30 seconds, 1, 2, 3, 5, 10, 20, 30 minutes or other desired periods of time 24 hours a day for an extended period of time). Certain embodiments disclosed provide for an improved and/or more detailed assessment of a patient's continually evolving circulatory state and response to treatment. Using certain disclosed systems results in many situations in a more cost effective treatment of the patient.

Using certain disclosed embodiments to achieve circulatory goals in a group of patients undergoing recovery from high risk surgery and/or shock will yield reduction in complications and/or decrease in ICU time and/or decrease in mortality and/or decrease in cost. Using certain disclosed embodiments to achieve circulatory goals in at least one patient undergoing recovery from high risk surgery and/or shock yields reductions in complications, decreased ICU time, decreased mortality and/or decreased cost.

One exemplary consequence of improved circulatory control is the reduction of side effects, for example, fluid overload; dehydration, pulmonary edema, atrial fibrillation and/or organ failure. These side effects are often the result of poor calibration and choice of therapy, such as IV saline, diuretics, pressors, etc. Frequently, the patient's circulatory system behaves in a counter-intuitive manner which results in poor therapy choices. One example would be when the patient's circulatory is under powered (i.e., low MAP and CO), fluid therapy may not always result in improved MAP and CO. Certain embodiments disclosed herein may reduce the frequency of this type of situation and the side effects which arise. A further consequence of the side effects is the need for additional therapy and time in intensive care to correct for the side effect. Not only does this discomfort the patient and expose them to the risk of long-term side effects, it substantially increases the cost of care.

Certain embodiments relate to systems and/or methods used to represent the subject's determined and/or present and desired circulatory states as a function of at least mean systemic filling pressure, heart efficiency and systemic vascular resistance as a on-screen, audio or data print-out representation.

Certain embodiments relate to systems and/or methods used to represent the subject's circulatory state and the subject's desired circulatory state as a function of mean systemic filling pressure, heart efficiency, systemic vascular resistance or combinations thereof. In certain aspects, these states will be represented in a two-dimensional graphical format. In certain embodiments, these states will be represented in three-dimensional and other graphical formats, such as bar chart or radial charts. In certain embodiments, representing the subject's circulatory state may often be accomplished by use of visual and/or audio means or combinations thereof.

Certain embodiments relate to systems and/or methods that may be used to determine a target direction and trajectory from the subject's present circulatory state to the subject's desired circulatory state on the two-dimensional, three-dimensional or other form of representation, wherein treatment of the subject so as to traverse said trajectory will cause the subject's mean arterial pressure (MAP) and cardiac output (CO)/oxygen delivery to converge to and/or move towards the subject's desired circulatory state. In certain embodiments, where the subject's oxygen saturation and hemoglobin levels are known, controlling the cardiac output will also cause the subject's oxygen delivery or venous oxygen to converge to a desired state. Said trajectory consists of the changes required in the individual treatments for volume, resistance and heart efficiency and the sequence of treatments needed.

Certain embodiments relate to systems and/or methods to visually representing the subject's actual and desired circulatory states as a function of mean systemic filling pressure, heart efficiency, and systemic vascular resistance as a two-dimensional representation and determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to, and/or move towards, the subject's desired circulatory state.

Certain embodiments are to computer-assisted methods, systems and/or devices for assessing a subject's circulation state, comprising at least one of the following steps: (i) determining said subject's present circulatory state using parameters sufficient to characterize the present circulatory state; and (ii) determining said subject's desired circulatory state using parameters sufficient to characterize the desired circulatory state. In certain aspects, the methods, systems and/or devices may be used for providing a treatment guidance for a subject. In certain aspects, the methods, systems and/or devices are used to measure the subjects circulation state. In certain aspects, a target direction is determined of a trajectory from the subject's present circulatory state to said subject's desired circulatory state. In certain aspects, where treatment guidance is desirable, the target direction and the trajectory are used to assisted in moving the subject's circulatory state along towards a desired circulatory state. In certain aspects, where treatment guidance is desirable, the target direction and the trajectory are used to assisted in providing treatment sequencing guidance in order to move said subject's circulatory state along towards a desired circulatory state. In certain aspects, the subject's present circulatory state is determined as a function of at least mean systemic filling pressure ($P_{ms}$), heart efficiency ($E_H$) and systemic vascular resistance (SVR). In certain aspects, the subject's desired circulatory state is determined as a function of at least mean systemic filling pressure ($P_{ms}$), heart efficiency ($E_H$) and systemic vascular resistance (SVR). In certain aspects, the subjects present circulatory state is continually determined. In certain aspects, the methods, systems and/or devices provide substantially continuous and/or intermittent guidance of said subjects circulatory state, and/or control of hemodynamic and oxygen management of the subject's circulatory system. In certain aspects, the methods, systems and/or devices provide substantially continuous and/or intermittent guidance of the subjects circulatory state, and/or control of hemodynamic and oxygen management of said subject's circulatory system. In certain embodiments, the methods, systems and/or devices provide substantially continuous and/or intermittent guidance of at least one of the following: fluid therapies for control of volume state, heart performance therapy, heart rate therapies, heart rhythm therapies and/or vasoactive therapies.

Various parameters may be used to characterize the subject's circulatory state. Various combinations of parameters may be used with certain disclosed embodiments. For example, in certain embodiments, at least MAP, RAP and CO are used to determine at least $P_{ms}$, $E_H$ and SVR. Other combinations of parameters and/or therapeutic targets are contemplated. For example, certain embodiments may target at least Oxygen delivery, as a function of at least CO. Certain embodiments may determine $P_{ms}$ from other combinations of variables. For example, RAP may be replaced by a measurement of venous pressure at a peripheral location. The MAP and CO terms may be replaced by a function of the arterial pressure waveform measured at a variety of locations. The patient's gender and other demographic variables may be used to derive variants to determine $P_{ms}$. When a known volume of fluid is administered, the change in $P_{ms}$, however determined, may be used to estimate the patient's systemic vascular compliance, which can provide methods for additional circulatory assessment and/or guidance. An alternate form of volume state measure other than $P_{ms}$ is the stressed vascular volume, which is Pms divided by the vascular compliance. Other embodiments provide for the circulation targets to be time varying. Other embodiments provide for targeting of derived variables, for example to keep SVR within a defined range or to keep Pms within a defined range.

Certain embodiments are to computer-assisted methods, systems and/or devices for assessing a subject's circulation state, comprising at least one of the following steps: (i) means for determining said subject's present circulatory state using parameters sufficient to characterize the present circulatory state; and (ii) means for determining said subject's desired circulatory state using parameters sufficient to characterize the desired circulatory state. In certain aspects, a means for determining a target direction of a trajectory from the subject's present circulatory state to said subject's desired circulatory state. In certain aspects, where treatment guidance is desirable, the target direction and the trajectory are used to assisted in providing a means for treatment sequencing guidance in order to move said subject's circulatory state along towards a desired circulatory state. In certain aspects, means for determining the subject's present circulatory state as a function of at least mean systemic filling pressure ($P_{ms}$), heart efficiency ($E_H$) and systemic vascular resistance (SVR).

Certain embodiments are to computer-assisted methods, systems and/or devices for providing therapeutic guidance of a subject's circulatory state, said method comprising the steps of: (i) determining said subject's present and desired circulatory states as a function of at least mean systemic filling pressure ($P_{ms}$), heart efficiency ($E_H$) and systemic vascular resistance (SVR); (ii) determining a target direction of a trajectory from said subject's present circulatory state to said subject's desired circulatory state, wherein treatment of said subject so as to traverse said trajectory will cause said subject's circulatory state to move towards a desired circulatory state; and (iii) visually representing the target direction of said trajectory to assist in the treatment. In certain aspects, a treatment sequencing guidance is provided. In certain aspects, steps (i) to (iii) are performed repeatedly based on updated values of said subject's present and/or desired state. In certain aspects, the treatment of the subject so as to traverse the trajectory will cause the subject's mean arterial pressure (MAP) and cardiac output (CO) to converge to the subject's desired circulatory state. In certain embodiments, the methods, systems and/or devices provide for substantially continuous. In certain embodiments, the methods, systems and/or devices provide for intermittent guidance. In certain embodiments, substantially continuous and/or intermittent guidance of the subjects circulatory state and/or control of hemodynamic and oxygen management of the subject's circulatory system is provided. In certain embodiments, substantially continuous and/or intermittent guidance of at least one of the following: fluid therapies for control of volume state, heart performance therapy, heart rate therapies, heart rhythm therapies and/or vasoactive therapies is provided.

Certain embodiments disclose a computer program product comprising a computer readable medium comprising a computer program recorded therein for assessing a subject's circulation state, said method comprising, said computer program product comprising: (i) computer program code means for assisting in the determination of said subject's present circulatory state using parameters sufficient to characterize the present circulatory state; (ii) computer program code means for assisting in the determination of said subject's desired circulatory state using parameters sufficient to characterize the desired circulatory state; (iii) computer program code means for visually representing said subject's present and desired circulatory states; (iv) computer program code means for determining a target direction of a trajectory from said subject's present circulatory state to said subject's desired circulatory state, wherein treatment of said subject so as to traverse said trajectory will cause said subject's mean arterial pressure (MAP) and cardiac output (CO) to converge to said subject's desired circulatory state; and (v) computer program code means for visually representing the target direction of said trajectory. In certain aspects, the computer program product further comprising computer program code means for executing said computer program code means (i) to (v) repeatedly based on updated values of said subject's present and/or desired state. In certain aspects, the computer program product provides computer program code means for determining a trajectory comprising: (vi) computer program code means for projecting MAP and CO isograms of said subject's present mean arterial pressure (MAP) and present cardiac output (CO) on said visual representation; (vii) computer program code means for bisecting an inner angle subtended by intersecting MAP and CO isograms, said inner angle in the quadrant the desired patient state is in; and (viii) computer program code means for selecting the bisection of said inner angle as the target direction of said trajectory. In certain aspects, the computer program product provides for computer program code means for visually representing a target range for the subject's MAP and CO. In certain aspects, the computer program product further comprises computer program code means for controlling an infusion rate of a medication administered to the subject in accordance with the trajectory.

Certain embodiments provide a circulatory monitoring and guidance system, comprising: a data acquisition unit; a visual display unit; a memory unit for storing data and instructions to be performed by a processing unit; and a processing unit coupled to said data acquisition unit, said visual display unit and said memory unit, said processing unit programmed to: (i) obtain subject specific parameters based on anthropometric data; (ii) acquire measured values of variables relating to said subject's circulation via said data acquisition unit; (iii) compute values of mean systemic filling pressure ($P_{ms}$), heart efficiency ($E_H$) and systemic vascular resistance (SVR) for said subject based on said subject specific parameters and said measured values; (iv) visually display said subject's present and desired circulatory states as a function of mean systemic filling pressure ($P_{ms}$), heart efficiency ($E_H$) and systemic vascular resistance (SVR) on said visual display unit; (v) determine a target direction of a trajectory from said subject's actual circulatory state to said subject's desired circulatory state, wherein treatment of said subject so as to traverse said trajectory will cause said subject's mean arterial pressure (MAP) and cardiac output (CO) to converge to said subject's desired circulatory state; and (vi) visually display the target direction of said trajectory on said visual display unit. In certain aspects, the circulatory monitoring and guidance system the processing unit is programmed to execute steps (i) to (vi) repeatedly based on updated values of the subject specific parameters and the measured values. In certain aspects, the processing unit is programmed to represent systemic vascular resistance (SVR) as an abscissa, mean systemic filling pressure ($P_{ms}$) as a primary ordinate and heart efficiency ($E_H$) as a secondary ordinate on said two-dimensional representation. In certain aspects, the processing unit is programmed to control an infusion rate of a medication administered to said subject in accordance with said trajectory.

Certain embodiments disclose a computer-assisted method for assessing a subject's circulation state, the method comprising: (i) deriving at least the subject's present mean systemic filling pressure ($P_{ms}$), heart efficiency ($E_H$) and systemic vascular resistance (SVR) from measurements of at least the subjects MAP, CO and RAP; (ii) deriving for the subject at least targeted mean systemic filling pressure ($P_{ms}$), heart efficiency ($E_H$) and systemic vascular resistance (SVR) values from at least target values of MAP, CO and RAP; (iii) determining for the subject a desired target direction of a trajectory from said subject's present state to said subject's desired state, wherein treatment of said subject so as to traverse said trajectory will cause said subject's circulatory state to move towards a desired circulatory state. In certain aspects, the computer-assisted method provides for substantially continuous and/or intermittent guidance and/or control of hemodynamic and oxygen management of said subject's circulatory system. In certain aspects, the computer-assisted method is used for circulatory state management. In certain aspects, the computer-assisted method is used to provide substantially continuous and/or intermittent guidance of at least one of the following: fluid therapies for control of volume state, heart performance therapy, heart rate therapies, heart rhythm therapies and/or vasoactive therapies. In certain aspects, the computer-assisted method is used to determine therapeutic changes on a continuous and/or intermittent guidance basis of at least one of the following volume state, heart performance, heart rate, heart rhythm and/or constriction or dilation of blood vessels.

Certain embodiments provide systems, methods and/or devices that may used in a closed loop control system, open loop control system, or combinations thereof. Certain embodiments may be used in a closed loop control system of intravenous and syringe pumps for volume, vasoactive and/or heart treatments.

Certain embodiments related to systems and/or methods including means for representing the subject's determined and desired circulatory states as a function of systemic filling pressure, heart efficiency and systemic vascular resistance as a two-dimensional representation. In certain embodiments, a minimal amount of information may be used to determine circulatory states. For example, in certain embodiments, only systemic filling pressure and vascular resistance can be used. As will be discussed in more detail below, this minimal information may in certain situations be less desirable since it may not allow for distinguishing whether volume or cardiac treatment is needed. Thus in certain situations, a more desirable representation may include heart efficiency. In the case of the latter, we have later defined heart efficiency in terms of mean systemic filling pressure (Pms) and right atrial pressure (RAP). There may be other forms of this function that may be used as well. Additional factors may also be included, for example, but not limited to, the volume responsiveness parameters. The graphical display may be extended to include other variables such as heart rate or intracranial pressure. In certain embodiments, the display may depict isograms for the target MAP and CO ranges. The CO range may also be depicted as a cardiac index (CI) range or oxygen delivery (DO2I) range. Means for representing the subject's circulatory state may often be accomplished by use of at least one visual, at least one audio or combinations thereof.

Certain embodiments are to computer-assisted methods and/or systems for assessing a subject's volume responsiveness state, the methods and/or systems comprising at least one of the following steps: (i) determining the subject's present volume responsiveness state as a function of at least mean systemic filling pressure ($P_{ms}$) and heart efficiency ($E_H$); and (ii) determining the subject's desired volume responsive state as a function of at least mean systemic filling pressure ($P_{ms}$) and heart efficiency ($E_H$). In certain aspects, the computer assisted methods and/or systems are used for providing a treatment guidance for the subject. In certain aspects, the computer-assisted methods and/or systems a target direction is determined of a trajectory from the subject's present volume responsiveness state to the subject's desired volume responsiveness state. Certain embodiments are to computer-assisted methods and/or systems wherein the treatment guidance, the target direction and the trajectory are used to assist in providing treatment sequencing guidance in order to move the subject's volume responsiveness state along towards a desired volume responsiveness state. In certain embodiments, the subject's present state and/or the subject's desired state are visually represented. In certain aspects, the computer-assisted methods and/or systems provide that the subjects present volume responsive state and/or the subjects desired volume responsiveness may be continually determined. In certain embodiments, the computer-assisted methods and/or systems provides substantially continuous and/or intermittent guidance of the subjects volume responsive state.

Certain embodiments are to computer-assisted methods and/or systems for assessing at least one of a subject's power volume responsiveness and cardiac output volume responsiveness, said methods and/or systems comprising: (i) determining at least one of said subject's present power volume responsiveness and present cardiac output volume responsiveness using parameters sufficient to characterize at least one of said subject's power volume responsiveness and cardiac output volume responsiveness; and (ii) determining at least one of said subject's desired power volume responsiveness and desired cardiac output volume responsiveness using parameters sufficient to characterize at least one of said subject's power volume responsiveness and cardiac output volume responsiveness; wherein heart efficiency ($E_H$) is substantially constant. In certain aspects, the computer assisted methods and/or systems are used for providing a treatment guidance for said subject. In certain aspects, the computer assisted methods and/or systems may be used to measure at least one of said subject's power volume responsiveness state and cardiac output volume responsiveness state. In certain aspects, the computer-assisted methods and/or systems may be used wherein a target direction is determined of a trajectory from at least one of said subject's present power volume responsiveness state and present cardiac output volume responsiveness state to at least one of said subject's desired power volume responsiveness state and desired cardiac output volume responsiveness state. In certain embodiments, the computer-assisted methods and/or systems may be used wherein the treatment guidance, the target direction and the trajectory are used to assisted in moving at least one of said subject's present power volume responsiveness state and present cardiac output volume responsiveness state along towards at least one of a desired power volume responsiveness state and a desired cardiac output volume responsiveness state. In certain embodiments, the computer-assisted methods and/or systems may be used wherein the treatment guidance, the target direction and the trajectory are used to assisted in providing treatment sequencing guidance in order to move at least one of said subject's power volume responsiveness state and cardiac output volume responsiveness state along towards at least one of a desired power volume responsiveness state and a desired cardiac output volume responsiveness state. In certain aspects, the computer-assisted methods and/or systems provide that said subject's present state and/or said subject's desired state are visually represented. In certain embodiments, the computer-assisted methods and/or systems may be used wherein at least one of said subjects present power volume responsiveness state and present cardiac output volume responsiveness state and/or at least one of said subjects desired power volume responsiveness state and desired cardiac output volume responsiveness state is continually determined. In certain embodiments, the computer-assisted methods and/or systems provides substantially continuous and/or intermittent guidance of at least one of said subjects power volume responsiveness state and present cardiac output volume responsiveness state.

Certain embodiments relate to systems and/or methods including means for determining a target direction of a trajectory from the subject's determined circulatory state to the subject's desired circulatory state on the two-dimensional representation, wherein treatment of the subject so as to traverse said trajectory will cause the subject's mean arterial pressure (MAP) and cardiac output (CO)/oxygen delivery to converge to, and/or move towards, the subject's desired circulatory state.

Certain embodiments relate to systems and/or methods that include means for visually representing the subject's determined and desired circulatory states as a function of at least one mean systemic filling pressure, at least one heart efficiency, and at least one systemic vascular resistance as a two-dimensional representation and means for determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO)/oxygen delivery to converge to, and/or move towards, the subject's desired circulatory state.

Certain embodiments relate to systems, methods and devices for therapeutic maintenance, guidance and/or control of mammalian circulation using measurement, interpretation and/or therapy. Certain embodiments relate to computer-assisted methods for therapeutic guidance for controlling a subject's circulation. The methods may include visually representing the subject's actual and desired circulatory states as a function of mean systemic filling pressure, heart efficiency and systemic vascular resistance as a two-dimensional representation and determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to the subject's desired circulatory state. In certain aspects, the methods may further include visually representing the target direction of the trajectory on the two-dimensional representation. Certain embodiments relate to circulatory monitoring and guidance systems or devices that includes a data acquisition unit; a visual display unit; a memory unit for storing data and instructions to be performed by a processing unit; and a processing unit coupled to the data acquisition unit, the visual display unit and the memory unit. In some aspects, the processing unit may be programmed to obtain subject specific parameters based on anthropometric data; acquire measured values of variables relating to the subject's circulation via the data acquisition unit; compute values of mean systemic filling pressure, heart efficiency and systemic vascular resistance for the subject based on the subject specific parameters and the measured values; visually display the subject's actual and desired circulatory states as a function of mean systemic filling pressure, heart efficiency and systemic vascular resistance on the visual display unit; determine a target direction of a trajectory from the subject's actual circulatory state to the subject's desired circulatory state, wherein treatment of the subject so as to traverse the trajectory will cause the subject's mean arterial pressure (MAP) and cardiac output (CO) to converge to the subject's desired circulatory state; and visually display the target direction of the trajectory on the visual display unit.

In certain embodiments, the target direction of the trajectory may be visually represented as an arrow. In certain aspects, the method and/or methods may further include visually representing a target range for the subject's MAP and CO on the two-dimensional representation.

In certain embodiments, the method and/or methods may further include controlling an infusion rate of a medication administered to the subject in accordance with the trajectory.

BRIEF DESCRIPTION OF THE DRAWINGS

Features and advantages will become apparent from the following description of embodiments thereof, by way of example only, with reference to the accompanying drawings, in which:

FIGS. 33a-33d are exemplary illustrations of various physical arrangements of circulatory guidance systems and bedside monitors in accordance with certain embodiments;

DETAILED DESCRIPTION

This disclosure relates generally to systems, methods, devices and computer program products for providing maintenance, guidance and/or control of certain systems. Often these systems may be complex systems. Complex systems such as the cardiovascular system or the respiratory system provide data that is often hard to interpret properly in order to determine the appropriate course of action or treatment in view of the information provided. For example, a subject with hypertension may be treated with anti-hypertensives as a first line therapy. If the subject fails to respond, further observation and consideration may reveal that the subject is volume overloaded with a high cardiac output and the system may suggest the need to reduce volume state through diuresis. This action may reduce the blood pressure to normal levels.

In some aspects, this disclosure relates to, but is not limited to, systems, methods and devices for therapeutic maintenance, guidance and/or control of mammalian circulation using measurement, interpretation and/or therapy. Certain embodiments relate to computer-assisted methods for therapeutic guidance for controlling a subject's circulation. This may be used in a number of situations and settings such as hospitals, critical care units, general intensive care units, surgical intensive care units, specialist intensive care units, cardiac care units, high dependency units, emergency rooms, operating rooms, recovery rooms, emergency field situations and/or ambulances.

Figure 30:
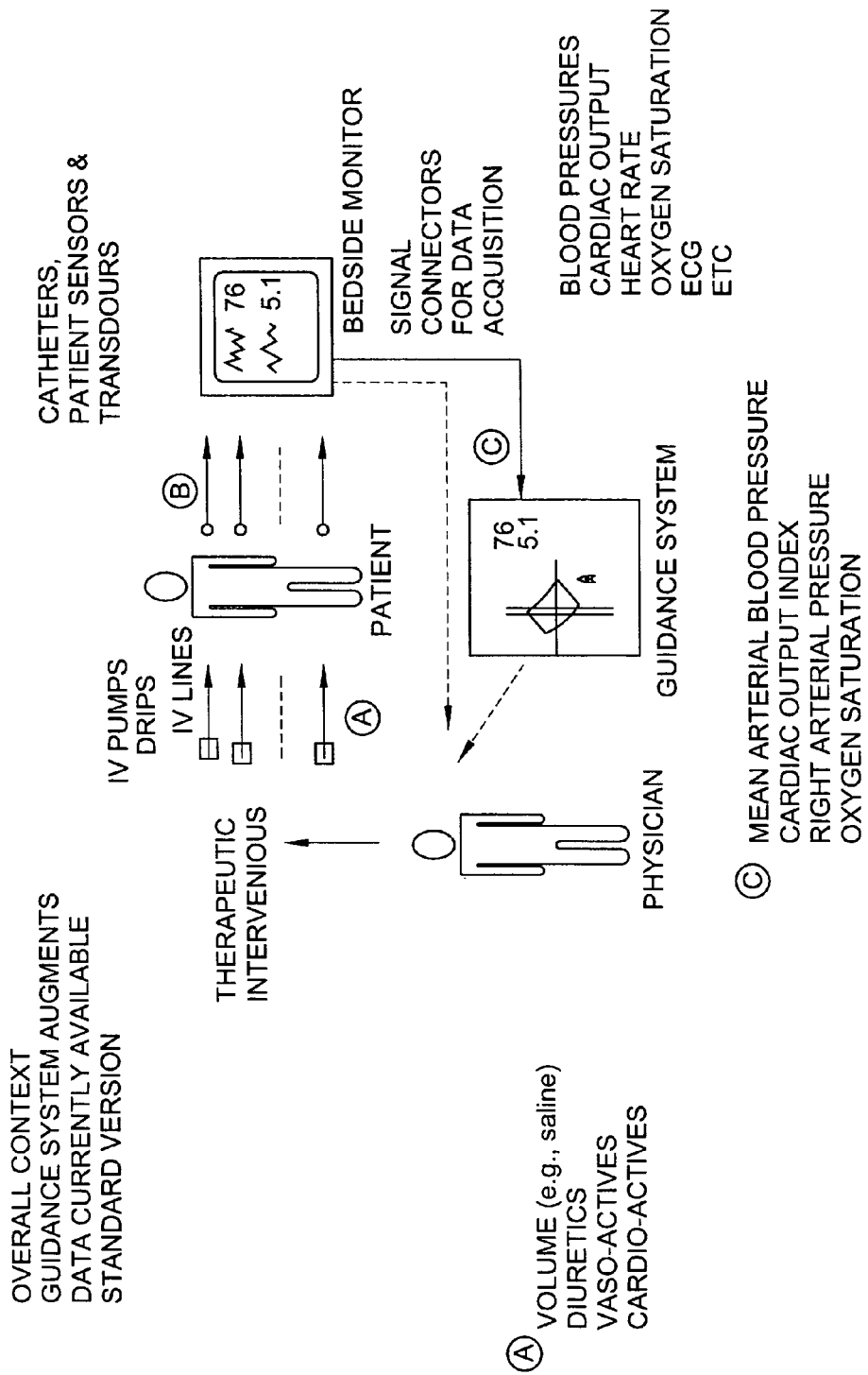
FIG. 30 is an exemplary illustration of a standalone circulatory guidance system in accordance with certain embodiments.

FIG. 30 illustrates the context for an exemplary system as a standalone circulatory guidance system. As shown, physiological variables are monitored using catheters, sensors and transducers attached to the patient and processed by a standard bedside monitor. Examples of such bedside monitors are Philips Intelliview, Draeger Infinity, Datex, GE Marquette and Spacelabs. An electrical signal cable (or wireless connection) may be made to the guidance system which enables it to acquire periodic data from the bedside monitor. The data acquired may include, for example, mean arterial pressure, cardiac output or index, right atrial pressure, heart rate, oxygen saturation. This exemplary embodiment provides means for user entry of additional patient data (e.g., height, age, weight and hemoglobin), representation of the patient state and desired state, and guidance on therapy required to achieve the desired state to a clinical user, usually nurse or physician. The user takes the guidance information along with other data to make a decision about therapy and to initiate or change therapy. Circulatory therapy is usually administered via controlled N drips, pumps or syringe pumps that are adjusted by the nurse. The care giver may issue orders for therapies. Circulatory therapies may include volume (e.g., saline, blood, and/or colloid), diuretics, vaso-actives and/or cardio-actives.

Figure 31:
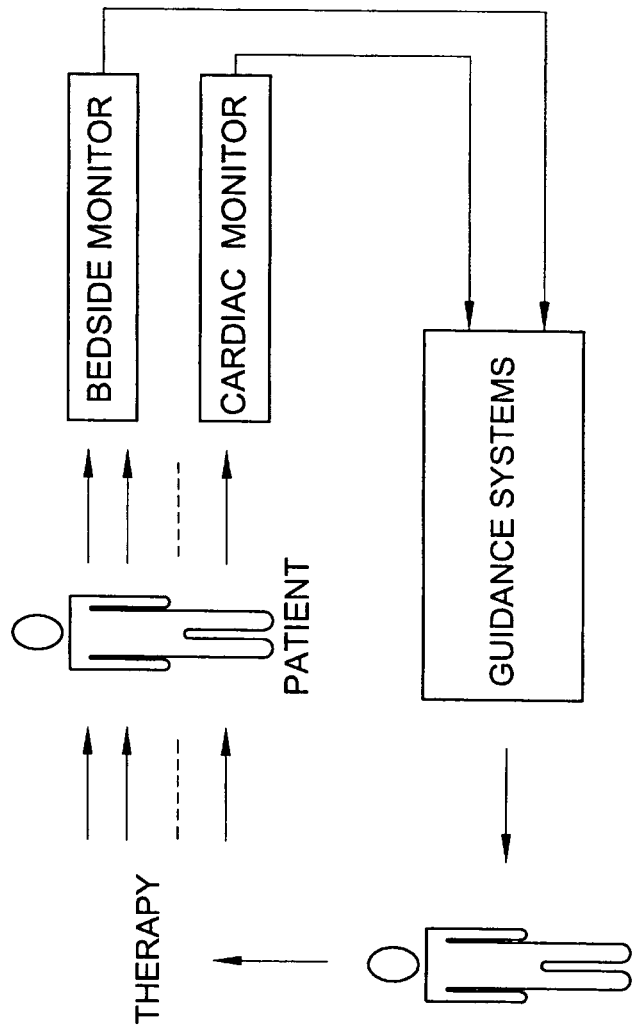
FIG. 31 is an exemplary illustration of a circulatory guidance system coupled to a bedside monitor and specialist cardiac monitor in accordance with certain embodiments.
Figure 32:
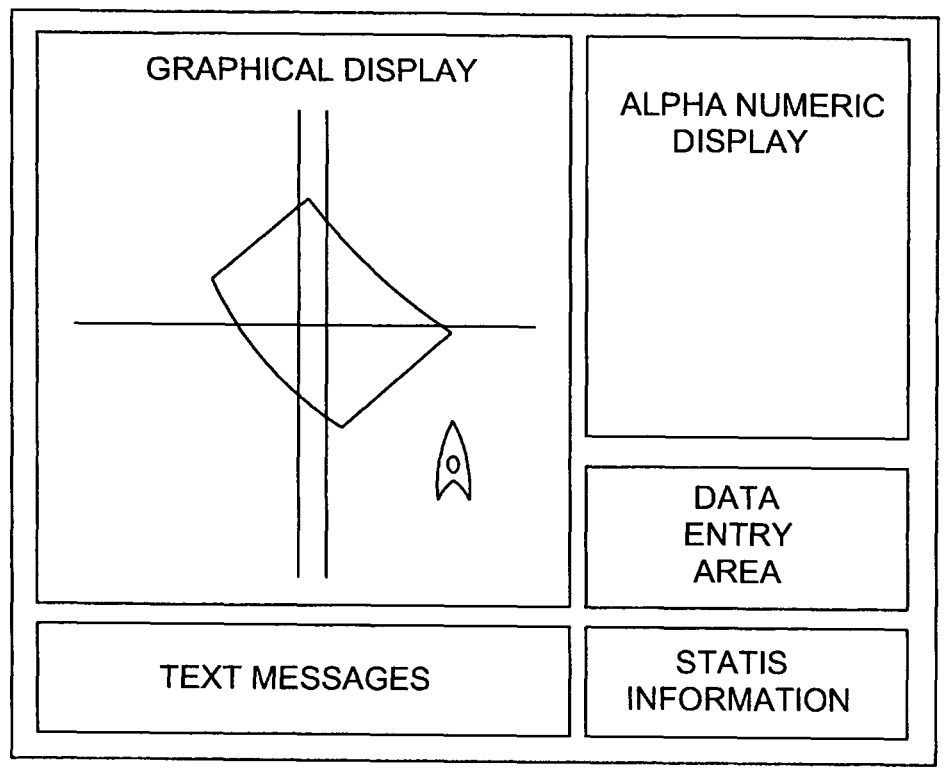
FIG. 32 is an exemplary illustration of a configuration of a visual display of a circulatory guidance system in accordance with certain embodiments.

FIG. 31, illustrates an embodiment where the guidance system is connected to a bedside monitor and to a specialist cardiac output monitor. Examples of such cardiac output monitors may include Edwards Vigileo, Edwards Vigilance, Pulsion PiCCO, Arrow OptiQ and LiDCO. FIG. 32 illustrates a configuration of components of a visual display for an exemplary embodiment of a circulatory guidance system including graphical, alphanumeric, data entry, status information and text message items, or combinations thereof. In certain embodiments, the computer program for the circulatory guidance system may run on the computer processing elements of a bedside monitor and/or cardiac output monitor. In certain embodiments a circulatory control system could automatically control the infusion rate of IV pumps and syringes without need for user intervention. Additionally, all, or some, of the visual display components of FIG. 32 may appear on the visual display unit of the said monitor or on another monitor.

Figure 1:
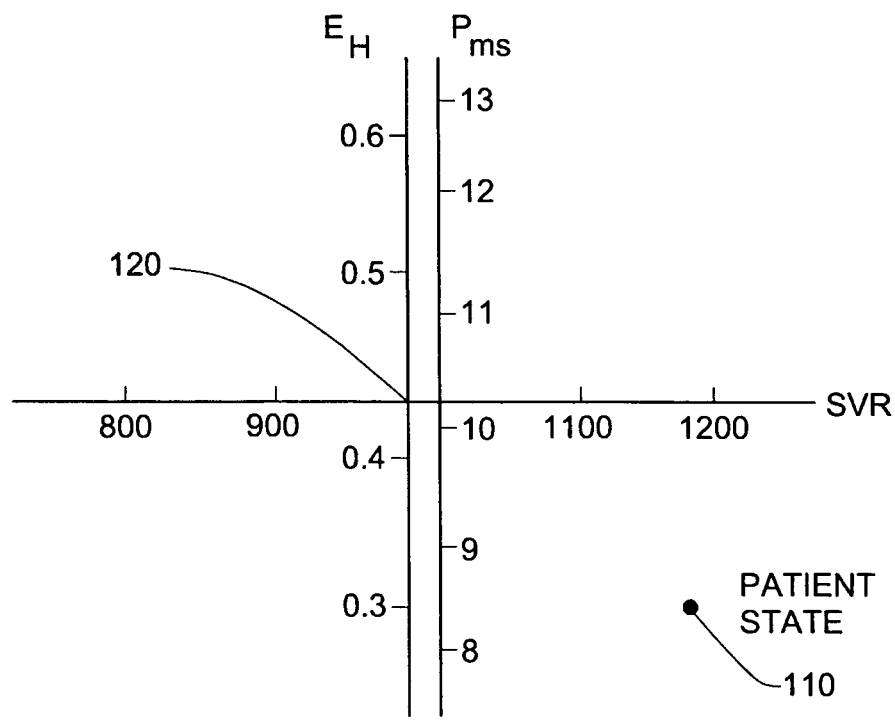
FIG. 1 is a 2-dimensional $\{P_{ms}, SVR\}$ graphical representation of the 3-dimensional $\{P_{ms}, E_H, SVR\}$ space in accordance with certain embodiments.
Figure 2:
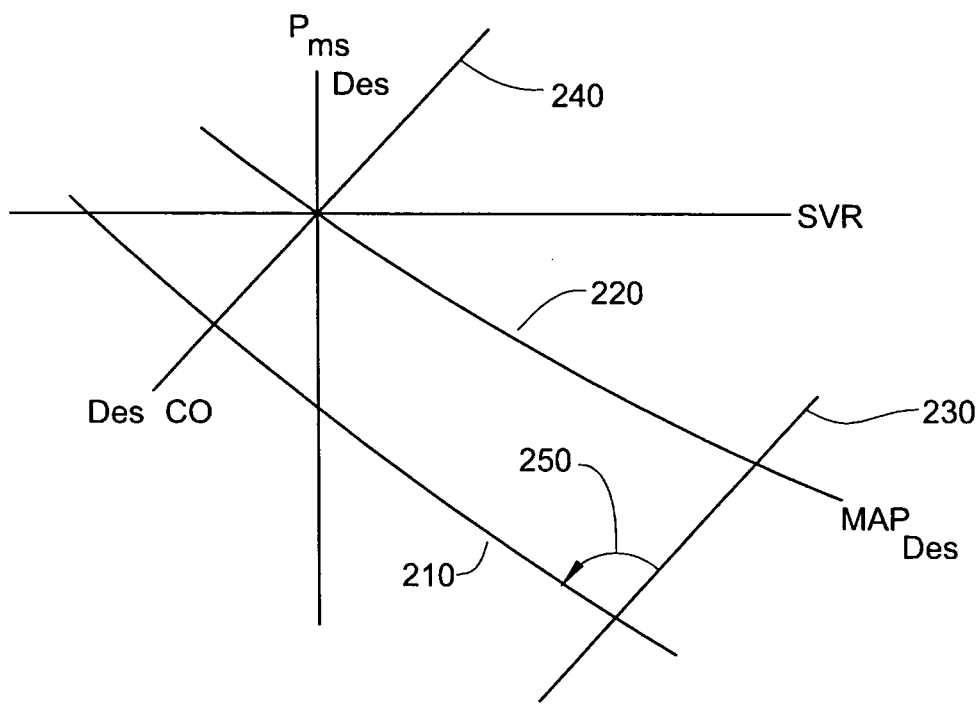
FIG. 2 shows MAP and CO isograms projected on the $\{P_{ms}, SVR\}$ space of FIG. 1 in accordance with certain embodiments.

For example, FIGS. 33a-33d illustrate various exemplary embodiments for physically arranging the guidance system with the bedside monitor FIG. 33a illustrates the guidance system as a free standing computing device with power supply, screen, i/o ports, computing hardware etc. The device communicates with standard monitor using serial, USB, Ethernet, wireless, etc using monitor vendor specific protocols and has data entry device such as mouse, keyboard, touch screen, thumbwheel or combinations thereof to introduce external data into fields. FIGS. 33b1 and 2 illustrate arrangements where the computing device is on a board with power supply external to but connected to the host monitor and the output is transmitted to a window or screen on the host monitor (FIG. 33b1). In this case, the circulation guidance screen is shared with the conventional monitor screen. Or, as illustrated in FIG. 33b2 a free standing screen may be provided which might be physically separated from the computing device. As illustrated in FIG. 33c, arrangements where the guidance software is installed within the standard monitor may also be provided or, as illustrated in FIG. 33d, the guidance software may exist in a subsidiary monitor. For example, the system of FIG. 33d may be provided where the cardiac output is measured with a stand alone instrument separate from the standard bedside monitor. The guidance software could then run within the cardiac output monitor. Such arrangements save on separate power supplies, boards, screens, reduce around bed cables and/or clutter. The instruments may have a symbiotic relationship as the guidance system needs the cardiac output and the cardiac output needs the guidance system for its proper use. The cardiac output monitor may support the communications and software to the standard monitor. In general, the circulation guidance system, particularly the design and operation of the screen is described throughout this disclosure and generally embraces control of the various (e.g., 2 or 3) states required to determine the circulatory dynamics. Additionally, volume responsiveness (also described herein) may be used chose between volume therapy and cardioactive medications.

Certain disclosed systems and/or methods may include, but are not limited to, representing the subject's actual and desired circulatory states as a function of mean systemic filling pressure, heart efficiency and systemic vascular resistance as a visual or audio representation. Visual representations may take the form of bar charts, radial plots, X-Y relational plots or time series charts. In certain embodiments it is desirable for the representation to have the ability to depict the three quantitative components of mean systemic filling pressure, heart efficiency and systemic vascular resistance. One approach is to use a modified X-Y relational plot in which SVR is on one of the axes and $P_{ms}$ is on the other axis, with the $E_h$ scale plotted parallel to the $P_{ms}$ scale, but moving relative to it. Further exemplary representations may be 3-dimensional. Additional variables (directly measured or derived) pertaining to the circulation may be included on these graphical, or other, representations for example volume responsiveness, blood pressure, heart rate, intracranial pressure, cardiac output, right atrial pressure, oxygen delivery, etc., or combinations thereof. These variables may be represented graphically or as textual labels. In some embodiments, no graphical information is displayed however guidance on therapeutic intervention is provided in natural language, displayed as text on screen or as audio. In some embodiments, only $P_{ms}$ and SVR are used.

In certain embodiments, the representation of the subjects existing status and the target status may be accomplished by use of a variety of visual, audio, or combination means. In certain aspects, the representation of the subject's circulatory state may often be accomplished by use of visual, audio or combinations thereof. Certain disclosed systems and/or methods may include, but not limited to, determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to, and/or move towards, the subject's desired circulatory state.

Certain systems and/or methods may include, but are not limited to, visually representing the subject's present and desired circulatory states as a function of certain measured and/or calculated parameters and, if desired, presenting this information in a two-dimensional representation. Determining a target circulatory state for the subject based on certain measured and/or calculated parameters and, if desired, presenting this information in a two-dimensional representation. Providing a direction of a trajectory from the subject's present circulatory state to the subject's desired circulatory state and, if desired, presenting this information in a two-dimensional representation. Certain systems and/or methods may include, but are not limited to, means for visually representing the subject's present and desired circulatory states as a function of certain measured and/or calculated parameters and, if desired, presenting this information in a two-dimensional representation. Means for determining a target circulatory state for the subject based on certain measured and/or calculated parameters and, if desired, presenting this information in a two-dimensional representation. Means for providing a direction of a trajectory from the subject's present circulatory state to the subject's desired circulatory state and, if desired, presenting this information in a two-dimensional representation. For example, certain disclosed systems and/or methods may be used to visually represent the patient's circulatory states as a function of mean systemic filling pressure, heart efficiency, and systemic vascular resistance. The disclosed systems and/or methods may also be used to determining a target direction of a trajectory from the patient's actual circulatory state to the patient's desired circulatory state and to visually represent this information, wherein the recommended treatment of the patient may traverse a certain trajectory and may cause the subject's mean arterial pressure (MAP) and cardiac output (CO) to converge to, and/or move towards, the patient's desired circulatory state. It is to be understood that other combinations of measured and/or calculated parameters may be used. For example, cardiac index, oxygen delivery and oxygen delivery index, intracranial pressure, intracranial-arterial pressure difference and heart rate. Certain disclosed systems and/or methods may include, but are not limited to, visually representing the subject's actual and desired circulatory states as a function of mean systemic filling pressure, heart efficiency and systemic vascular resistance as a two-dimensional representation and determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to, and/or move towards, the subject's desired circulatory state.

Certain disclosed systems and/or methods may include means for representing the subject's determined and desired circulatory states as a function of systemic filling pressure, heart efficiency, and systemic vascular resistance as a two-dimensional representation. Means for representing the subject's circulatory state may often be accomplished by use of at least one visual, at least one audio or combinations thereof. Certain disclosed systems and/or methods may include means for determining a target direction of a trajectory from the subject's determined circulatory state to the subject's desired circulatory state on the two-dimensional representation, wherein treatment of the subject so as to traverse said trajectory will cause the subject's mean arterial pressure (MAP) and cardiac output (CO) to converge to, and/or move towards, the subject's desired circulatory state.

Certain disclosed systems and/or methods may include, but are not limited to, means for visually representing the subject's determined and desired circulatory states as a function of at least one mean systemic filling pressure, at least one heart efficiency and at least one systemic vascular resistance as a two-dimensional representation and means for determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to, and/or move towards, the subject's desired circulatory state.

Certain disclosed methods may include, but are not limited to, visually representing the subject's actual and desired circulatory states as a function of mean systemic filling pressure, heart efficiency and systemic vascular resistance as a two-dimensional representation and determining a target direction of a trajectory from the subject's actual circulatory state to the subject's desired circulatory state on the two-dimensional representation, wherein treatment of the subject so as to traverse said trajectory will cause the subject's mean arterial pressure (MAP) and cardiac output (CO) to converge to the subject's desired circulatory state. Certain embodiments relate to therapeutic maintenance, guidance and/or control of warm blooded animals.

It has been experimentally shown that a determinant of circulatory dynamics may be the mean systemic filling pressure ($P_{ms}$), defined as the pressure of an average element in the systemic circulatory network (i.e., between the high arterial pressures and low venous pressure). Historically and in current practice other measures are used to characterize the circulatory system which includes left and right heart pressures and volumes and intra-thoracic blood volume. However, these measures are cardio-centric and do not account for the dynamics in the systemic circulation and the pressures driving venous blood to return to the heart. $P_{ms}$ can also be defined in certain situations as the pressure that the whole circulation would achieve if the heart stopped. The reason that $P_{ms}$ may be useful in certain embodiments is that it is the pressure driving the return of blood to the right side of the heart, the venous return (VR). According to Starling's Law, the heart will adjust to pump out blood it receives and hence match cardiac output (CO) to VR. Thus $P_{ms}$ may be a determinant of CO, one of the key measures of adequate circulatory function. Surprisingly, the impact of this finding on the clinical management of circulatory control has been negligible because of the lack of a means, and or desire, to measure $P_{ms}$.

However, based on dynamic mathematical modeling of the cardiovascular system it can be demonstrated that $P_{ms}$ may be estimated in an "analog" form ($P_{msa}$) given certain measurements (e.g., measurements of mean arterial pressure (MAP), right atrial pressure (RAP) and cardiac output (CO) and taking into account the age and size of the subject). In certain embodiments, the estimate may be:

$$P_{msa} = f(\text{RAP}, \text{MAP}, \text{CO}, c) \tag{1},$$

where c is a coefficient dependent on age and size.

More specifically, in certain embodiments, the following linear equation may be an accurate estimate of the analogue form of the above equation, $$P_{msa} = a\text{RAP} + b\text{MAP} + c(\text{age}, \text{size})\text{CO} \tag{2},$$

where a and b are fixed coefficients for the subjects.

An additional measure of heart effectiveness $E_H$ can also be introduced:

$$E_H = \frac{P_{ms} - \text{RAP}}{P_{ms}} \tag{3}$$

$E_H$ may have the characteristic of being bounded by zero and unity in certain embodiments. When the heart is failing, RAP may rise, thereby decreasing $E_H$. When the heart stops, all pressures may be substantially equal to $P_{ms}$ and hence $E_H$ may be substantially equal to zero. In a normally functioning heart RAP is about zero, and hence $E_H$ equals about one. In certain embodiments, the analogue form of equation (1) may be needed to compute equation (2). In certain embodiments, $E_H$ may be a measure of how well the heart is performing in the current circulation. In certain equivalent embodiments a different mathematical function may be used, using the $P_{ms}$ to right atrial pressure difference and the current value of $P_{ms}$.

The measurement of $P_{ms}$, or volume state, is useful in many of the disclosed embodiments because this measurement enables the design and use of guidance, or closed-loop control, systems for use in critical care. Certain embodiments relate to systems, methods and devices for maintenance, guidance and/or control of certain systems for use in critical care wherein $P_{ms}$, is measured or determined as part of the use of the system, method and device. Certain embodiments relate to systems, methods and devices for therapeutic maintenance, guidance and/or control of mammalian circulation using measurement, interpretation, and/or therapy wherein $P_{ms}$, is measured or determined as part of the use such systems, methods and devices. Certain embodiments relate to computer-assisted methods for therapeutic guidance for controlling a subject's circulation wherein $P_{ms}$, is measured or determined as part of the use of such computer assisted methods.

The measurement of $E_H$, or inotropy, is useful in many of the disclosed embodiments because this measurement enables the design and use of guidance, or closed-loop control, systems for use in critical care. Certain embodiments relate to systems, methods and devices for maintenance, guidance and/or control of certain systems for use in critical care wherein $E_H$, is measured or determined as part of the use of the system, method, and device. Certain embodiments relate to systems, methods and devices for therapeutic maintenance, guidance and/or control of mammalian circulation using measurement, interpretation, and/or therapy wherein $E_H$, is measured or determined as part of the use such systems, methods, and devices. Certain embodiments relate to computer-assisted methods for therapeutic guidance for controlling a subject's circulation wherein $E_H$ is measured or determined as part of the use of such computer assisted methods.

The measurement or determination of $P_{ms}$ and $E_H$ are useful in many of the disclosed embodiments because these measurements or determinations enable the design and use of guidance, or closed-loop control, systems for use in critical care. Certain embodiments relate to systems, methods and devices for maintenance, guidance and/or control of certain systems for use in critical care wherein $P_{ms}$ and $E_H$ are measured or determined as part of the use of the system, method and device. Certain embodiments relate to systems, methods and devices for therapeutic maintenance, guidance and/or control of mammalian circulation using measurement, interpretation and/or therapy wherein $P_{ms}$ and $E_H$ are measured or determined as part of the use such systems, methods, and devices. Certain embodiments relate to computer-assisted methods for therapeutic guidance for controlling a subject's circulation wherein $P_{ms}$ and $E_H$ are measured or determined as part of the use of such computer assisted methods.

The measurements of mean arterial blood pressure (MAP), cardiac output (CO) and right atrial pressure (RAP) reflect the conjoint effects of the different circulatory functions and corresponding therapeutic modalities. For example, if MAP is low this may be due to a low volume state or to inadequate heart function. Thus a low MAP could indicate a need for volume therapy or inotropes (which increase the strength of cardiac contractions). The space defined by MAP, CO and RAP is one in which dimensions confound the effects of therapy.

Figure 34:
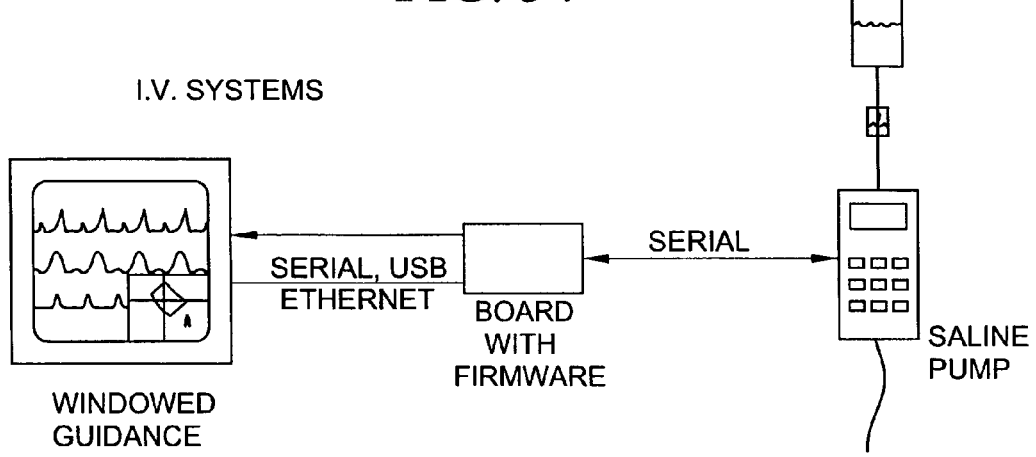
FIGS. 34-36 are exemplary illustrations for automated control systems (e.g., for i.v., blood pressure, and dialysis) and accordance with certain exemplary embodiments.

In certain embodiments, it may improve circulatory control to represent the subject's state in a space where the dimensions are congruent with single therapeutic effects. In such a "therapeutic space", it may be possible to assess and change therapies with numerical precision, which means arriving at the desired MAP and CO/oxygen delivery faster and more precisely (e.g., by selecting the correct modality as well as the amount). Such a space can form the basis for a clinical guidance system in which the therapy decision is made by the clinician and for schemes of closed-loop or automated control in which the therapy adjustments to intravenous or syringe pumps are made automatically. Such a space can form the basis for a clinical guidance system in which the therapy decision is made by the clinician and for schemes of substantially closed-loop or substantially automated control in which the therapy adjustments to intravenous or syringe pumps are made automatically, or semi-automatically, (as illustrated in FIG. 34 where the guidance system communicates with the saline pump.

Fluid therapy is one of the commonest therapies in hospital use. Perhaps 800 million liters of i.v. fluid are administered annually. Approximately ⅔ of that fluid is 5% dextrose, effectively water, which is administered to control tonicity or the ion concentration of the plasma. ⅓ of the fluid is N saline or a similar substance including plasma, the object of which is to control the volume state, i.e., P. A smart i.v. fluid system may call on $P_{ms}$ in a guidance or control role and not depend on fluid balance charts which are often ubiquitous, notoriously inaccurate and time consuming. They may incorporate tonicity controllers. Since $P_{ms}$ ultimately controls the power output of the heart (MAP*CO), the target $P_{ms}$ may be determined by the target power. If $P_{ms}$ is unknown and the patient is volume responsive, volume control may be slaved to circulation power. A special case for volume controllers exists in patients typically in advanced left or biventricular failure and/or renal failure. Such patients frequently become oedematous and haemofiltration can be used in their care. Volume guidance/controllers can be used to maintain the fine balance between "too wet" and "too dry".

Figure 35:
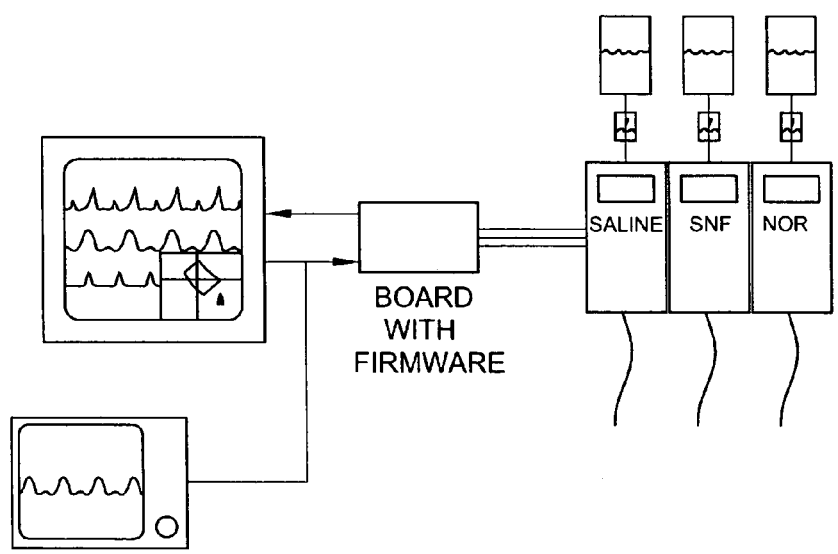

Additionally, in some environments there is a requirement to control MAP. This requires appropriate manipulation of volume, resistance and the heart. As shown in FIG. 35, the design of the controller includes devices to control high blood pressure, a common clinical requirement, to elevate MAP in special circumstances (see following) and occasionally to hold a low blood pressure (e.g., in hypotensive surgery under anaesthesia). An exemplary case of blood pressure control relates to patients with a high intracranial pressure (ICP) where the cerebral perfusion pressure (CPP) (CPP=MAP_ICP) must be maintained. Similar requirements for MAP elevation exist in patients with vasospasm causing neurological disturbance following subarachnoid haemmorrhage (SAH) or surgery for SAH. Blood pressure control both up and down may be required after surgery for phaechromocytoma (an adrenal tumour that excretes catecholamines.

Additionally, in certain embodiments an integrated control system may control IV pumps including those for volume, diuretics, vasoconstrictors, vasodilators and/or inotropes in order to provide closed-loop control for MAP and CO/oxygen delivery.

Figure 36:
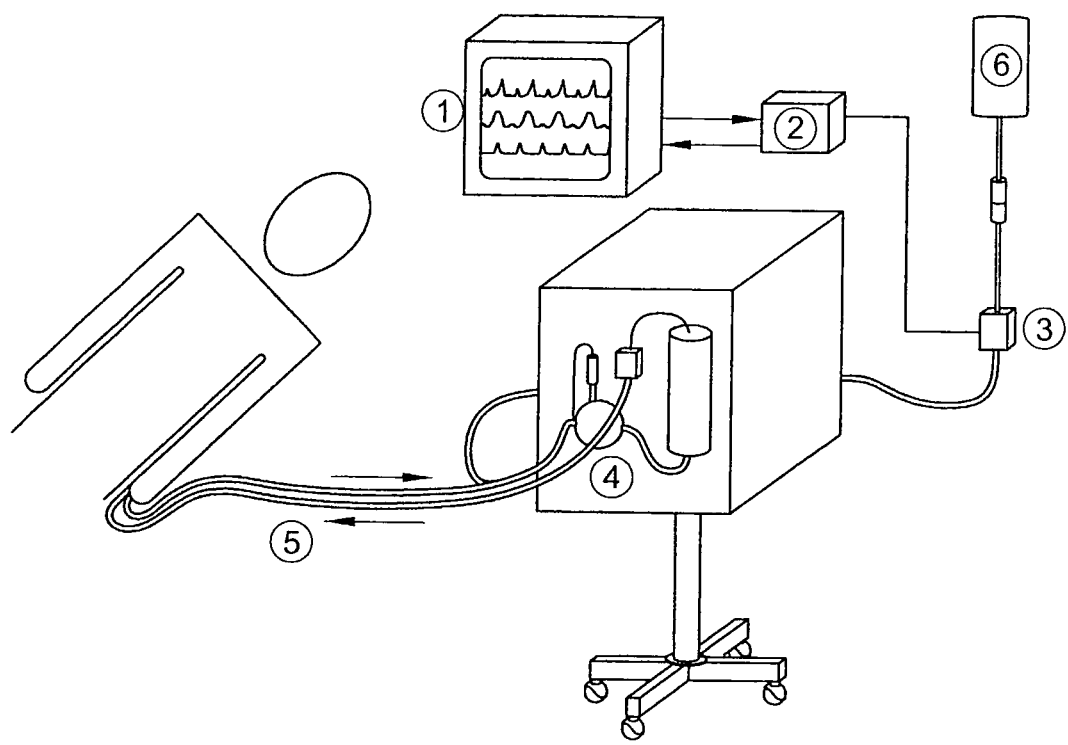

FIG. 36 illustrates an embodiment of a smart dialysis machines for volume guidance/control in dialysis. Typically dialysis machines are used in patients in renal failure to take over the function of the kidney. In addition to excreting waste products the kidney (and dialyser) must fulfill the function of controlling the volume state and tonicity in patients who are unable to pass urine. Tonicity control is achieved by dialyzing the patient against dialysis fluids which have a normal tonicity. The patient comes into tonic equilibrium with the dialyser. Volume ($P_{ms}$) control is normally achieved by dialyzing/filtering off fluid until the appropriate volume state is reached. In haemofiltration extra fluid may be taken off for the filtrative removal of wastes and replaced with pure saline. In a sick patient on dialysis maintaining the volume balance may be a demanding process. In some embodiments, $P_{ms}$ based volume controllers may be incorporated into dialysis machines so that the volume state may be guided or servo controlled. This is probably the first environment into which volume servo control will be introduced, the availability of dialysis to avoid the possibility of hazardous overshoots making it particularly safe. Equally the availability of circulation guidance and volume servo control may be a very useful adjunct to the management of the circulation in critically ill patients in renal failure, for example, patients in septic shock. Modern dialysis machines seek to maintain circulatory volume balance where volume in equals volume out strategy. This takes no account of the internal distribution of fluids and how much is lost to or gained from the interstitial or "third space" compartments. It is time for a more sophisticated approach. Rather than regulating the loss/gain of the dialyser by shifting the position of the zero transmembrane pressure point one can set the dialyser to lose fluid and then servo control volume replacement with a simple $P_{ms}$ controlled on/off clamp on a volume replacement line.

Further, the guidance system information may be useful for regulation of the circulation in patients in whom there is a heart/lung machine, ventricular assist device, artificial heart, etc. Unlike the normal heart, the output of which is servo controlled to the input, mechanical hearts are not thus regulated. A problem with ventricular assist devices for example has been "stalling" when the pump output is not matched by the venous return. Since $P_{ms}$ regulates the venous return, $P_{ms}$ based controllers may provide more understanding in the care of patients with mechanical hearts.

A canonical representation (e.g., one that reduces to simpler and significant form without loss of generality) is generally not possible without using the mean systemic filling pressure and heart efficiency derived variables as in equations (1) and (2). In certain embodiments, the dimensions of this new space may include:

1. analogue mean systemic filling pressure ($P_{msa}$), which relates to volume increasing or volume decreasing therapy;
2. heart efficiency ($E_H$), which relates to cardioactive therapies including inotropes, chronotropes and lusitropes; and
3. systemic vascular resistance (SVR), which relates to vasoconstrictor and vasodilator therapy and may be defined as:

$$SVR = \frac{80(MAP-RAP)}{CO} \quad (4)$$

dynes.cm$^{-5}$.sec

A position in the $\{P_{ms}, E_H, SVR\}$ space can be determined from equations (1) to (4) for both the patient's actual state $\{P_{ms}, E_H, SVR\}_{act}$ and a desired patient state $\{P_{ms}, E_H, SVR\}_d$. It is customary to prescribe the desired patient state in terms of MAP and CO (or oxygen delivery), but not RAP. By comparing the elements of $\{P_{ms}, E_H, SVR\}_{act}$ and $\{P_{ms}, E_H, SVR\}_{des}$, it is possible to assess the overall change required in each element (therapy modality) to achieve the desired therapy.

In certain embodiments, the 3-dimensional $\{P_{ms}, E_H, SVR\}$ space may be depicted in two dimensions without loss of, or substantial loss of, information. For example, as shown in FIG. 1, this may be achieved by plotting SVR as the abscissa (x-axis) and $P_{msa}$ as the primary ordinate (y-axis). Equation (2) may then used with the current RAP value to determine a second scale on the ordinate for $E_H$, as shown in FIG. 1. As RAP changes, the relationship between the $P_{msa}$ and $E_H$ scales changes (i.e., the scales move relative to each other). It should be noted that if $P_{msa}$ is a linear scale, then $E_H$ may be a non-linear scale. The symbol $P_{ms}$ in certain embodiments may be used for the analogue form $P_{msa}$. In certain embodiments, the 3 coordinates $\{P_{ms}, E_H, SVR\}$ space may be depicted in other 2 dimensional representations such as bar charts, polar or radial charts, multiple time series charts and in 3 dimensional representations. In certain embodiments, other numeric variables may be added to provide additional labeling or dimensions.

The current patient state 110 is indicated on the graph of FIG. 1. In certain embodiments, a useful way to draw FIG. 1 may be to position the center of the chart, where the axes cross, at the desired circulation or patient state 120. It is then apparent to the observer in what direction and by how much the 3 variables need to change in order to acquire the desired circulation. These three variables are volume state, systemic vascular resistance and heart efficiency. Without the system it is frequently hard to determine the needed changes and they do not always match clinical intuition. For example, without the system a low blood pressure and cardiac output may suggest need for volume therapy. With the system, it may become apparent whether cardiac inotropes are required instead, and whether vaso-active therapy is needed. A fall in $E_H$ to very low values (for example, an $E_H$<0.3 in humans) may indicate not only that the heart is failing, but that there may be other physical impediments impeding venous return or sufficient cardiac function. These may include abnormally high intra-thoracic pressure and cardiac tamponade. In clinical practice, differential diagnosis may be indicated for low $E_H$. Once physical impediments have been ruled out, a low $E_H$ can indicate the need for cardiac medications, including, but not limited to, inotropes, chronotropes, lusitropes or combinations thereof.

Having determined the distance from the actual position 110 to the desired position 120 on the 3 axes in the therapeutic space, it remains to determine the path of therapeutic maneuvers to achieve the desired circulation. For example, if a subject requires volume and vasodilatation which should be given first? Does the order of therapy matter? This can be described as the tactical problem—what to do now—whereas the overall change is the strategic problem. The tactical problem is non-trivial and it does not generally follow that all therapies should be given simultaneously and in direct line to the target. In fact, it may be dangerous to proceed in that direction. For example, a patient may need filling and vasodilatation. However, if they are dilated first with a low blood pressure, there is a risk of further drop in blood pressure and consequent shock and organ failure. In this case it is important to fill prior to dilating. The various embodiments disclosed provide methods for selecting the appropriate, or substantially appropriate, treatment sequencing decisions and avoiding, or substantially avoiding, the inappropriate ones. It is the avoidance, or substantial avoidance, of inappropriate treatment choices (and/or sequences) that enables the disclosed system(s) to provide better, or improved, circulatory care and reduced risk of side effects. The system(s) disclosed provide various means to determine the appropriate sequence and/or order of therapy. In practice, the subject's state may be continually changing and both strategic situational assessment and tactical treatment change may need constant re-consideration. These facts, coupled with the complex underlying circulatory dynamics, make this a challenging and non-trivial issue. The system provides a means to continuously assess the patient's state and select appropriate short and long term therapy in order to adjust to the changing patient condition and to the effects of treatment. It enables improved circulatory control and the avoidance of situations in which side effects can occur.

In certain embodiments, a method for solving this problem is to consider that the subject's current observed state is $\{MAP, CO\}_{act}$ and the desired state is $\{MAP, CO\}_{des}$. The aim of tactical therapy choice is to drive both MAP and CO monotonically closer to the desired state and to not move further away. Two steps are often required to determine an optimal trajectory to the desired state. First, project lines of constant MAP and CO/oxygen delivery on the $\{P_{ms}, SVR\}$ space (it is not necessary to consider $E_H$ as it is a function of $P_{ms}$). These lines are referred to as the MAP and CO isograms. Second, determine the optimal trajectory relative to the isograms to achieve the aim of tactical therapy. This method can be applied regardless of which graphical method of representation has been selected. The 2 dimensional X-Y relational plot depicted in FIG. 1 is a practical and usable representation for these purposes, but not the only one.

The isograms are derived from equations (1), (2) and (4) and express $P_{ms}$ as a function of SVR. These may be obtained from equation (1) using the SVR equation (3) to substitute for MAP or CO, respectively. The linear form of equation (2) may also be used.

The MAP isogram may be defined by:

$$P_{ms} = f_{MAP}(SVR, \overline{MAP}, RAP_{Act}, c) \quad (5)$$

Where, $\overline{MAP}$ denotes constant MAP for a given isogram; and $RAP_{Act}$ is the actual current measured value of RAP.

The linear form obtained by substituting into equation (2) may be:

$$P_{ms} = aRAP_{Act} + b\overline{MAP} + \frac{80c(\overline{MAP} - RAP_{Act})}{SVR} \quad (6)$$

The CO isogram may be defined by:

$$P_{ms} = f_{CO}(SVR, \overline{CO}, RAP_{Act}, c) \quad (7)$$

where $\overline{CO}$ denotes constant CO for a given isogram. The linear form may be:

$$P_{ms} = RAP_{Act} + c\overline{CO} + \frac{b\overline{CO} \cdot SVR}{80} \quad (8)$$

FIG. 2 shows MAP and CO isograms projected on the $\{P_{ms}, SVR\}$ space of FIG. 1 in accordance with certain embodiments disclosed herein. Isograms 210 and 220 are MAP isograms for the actual (Act) and desired (Des) patient states, respectively, and isograms 230 and 240 are CO isograms for the actual (Act) and desired (Des) patient states, respectively.

Usually a trajectory contained within the inner angle between the MAP and CO isograms will take both variables closer towards their target values. As shown in FIG. 2, the inner angle 250 is the angle in the quadrant containing the desired target state. An effective exemplary solution, which provides a locally optimal therapeutic guidance trajectory, is to bisect the inner angle. If a variable is close to or on its target, then the optimal guidance trajectory typically will follow along the isogram relating to that variable in the direction which takes the other variable closer to its target. This may be accomplished by using weighting functions in combining the angles that take into account the proportional distance from the desired target values of each of the variables. Specifically, in an exemplary embodiment, a computer-assisted method/computer program/system for determining the optimal treatment for volume, resistance and heart based on projecting lines of constant MAP and CO onto a geometric space with the coordinates of $P_{ms}$ and SVR, with the angles formed between the intersecting MAP and CO lines and consideration of the location of the target indicating the optimal treatment may be used. The value of $E_h$ may be used to assist in determining whether volume or heart therapy is required or both. A correction is made to allow for the closeness of MAP and CO to their target values. In general the basis of this algorithm is abstract geometry and the mapping between a $\{MAP, CO\}$ space and a $\{Pms, Eh\}$ space.

Figure 3:
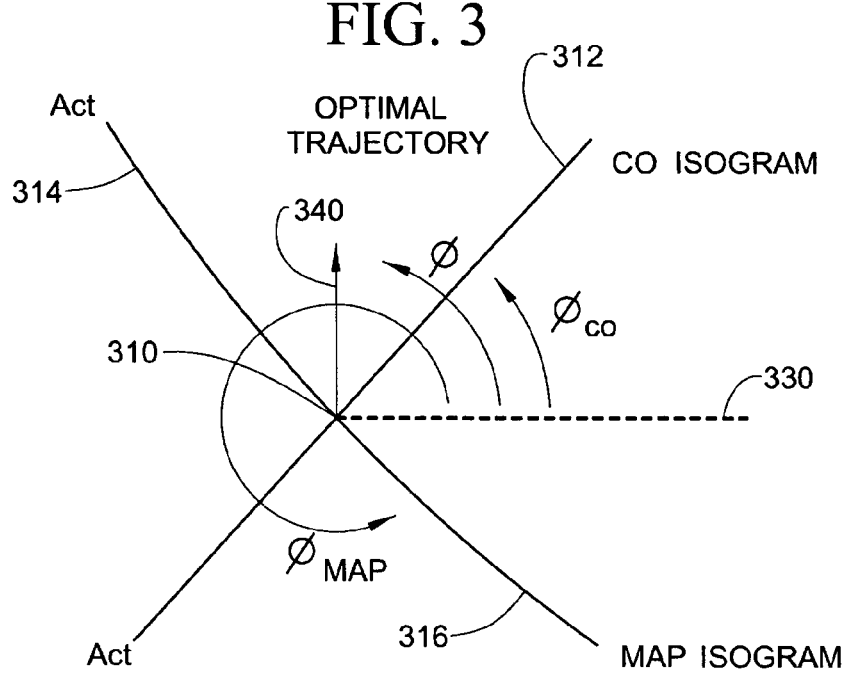
FIG. 3 shows geometrical determination of an optimal trajectory using the 2-dimensional $\{P_{ms}, SVR\}$ graphical representation of FIGS. 1 and 2 in accordance with certain embodiments.

An embodiment for determining the optimal trajectory is described with reference to FIG. 3. Referring to FIG. 3, a subject's actual circulatory state 310 and desired circulatory state 320 are shown as points on the $\{P_{ms}, SVR\}$ space. Actual CO and MAP isograms 312 and 314, respectively, intersect at the subject's actual circulatory state 310. $\phi_{CO}$ is the acute angle formed between the CO isogram 312 and the horizontal 330. $\phi_{MAP}$ is the obtuse angle formed between the MAP isogram 314 (or a tangent 316 to the MAP isogram 314 at the subject's actual circulatory state 310) and the horizontal 330. The optimal guidance trajectory 340 may be specified by a vector at an angle θ to the horizontal 330. Algorithmic steps for determining the optimal trajectory may be as follows:

1. Compute $\phi_{CO}$
2. Compute $\phi_{MAP}$
3. Compute weighting functions $\omega_{CO}$ and $\omega_{MAP}$
4. Adjust for inner angle (depending on position relative to target)
5. Compute the optimal guidance trajectory using:

$$\theta = \frac{\omega_{MAP}\phi_{CO} + \omega_{CO}\phi_{MAP}}{\omega_{MAP} + \omega_{CO}} \quad (9)$$

In certain embodiments, this approach may be beneficial since the patient state may evolve moment-to-moment and the guidance trajectory may change.

A specific realization of the foregoing algorithmic steps using equations (6) and (8) for the isograms, the method of bisection of the inner angle, and a hyperbolic tangent as weighting function is:

$$\phi_{CO} = \tan^{-1}(bCO) \quad (10)$$

$$\phi_{MAP} = 2\pi - \tan^{-1}\left[\frac{c(MAP_{Act} - RAP_{Act})}{(SVR/80)^2}\right] \quad (11)$$

$$\omega_{CO} = \tanh\left[\beta\left|\left(\frac{CO_{Act} - CO_{Des}}{CO_{Des}}\right)\right|\right] \quad (12)$$

$$\omega_{MAP} = \tanh\left[\beta\left|\left(\frac{MAP_{Act} - MAP_{Des}}{MAP_{Des}}\right)\right|\right] \quad (13)$$

Typically, $\beta=20$

Adjustments for the inner angle:

$$MAP_{Act} > MAP_{Des} \Rightarrow \phi_{CO} \leftarrow \phi_{CO} + \pi \quad (14)$$

$$CO_{Act} < CO_{Des} \Rightarrow \phi_{MAP} \leftarrow (\phi_{MAP} + \pi) \bmod 2\pi \quad (15)$$

$$CO_{Act} > CO_{Des} \cap MAP_{Act} < MAP_{Des} \Rightarrow \phi_{MAP} \leftarrow \phi_{MAP} - 2\pi \quad (16)$$

The optimal tactical guidance trajectory may be given by:

$$\theta = \frac{\omega_{MAP}\phi_{CO} + \omega_{CO}\phi_{MAP}}{\omega_{MAP} + \omega_{CO}} \quad (17)$$

As a vector in the $\{P_{ms}, E_H, SVR\}$ space, θ resolves into the required therapeutic changes in each of these dimensions. The θ vector can be depicted as a "compass" arrow on the $\{P_{ms}, E_H, SVR\}$ chart for guidance, determine the direction of therapy on bar charts, other visual representations, or can be used as the input into a closed loop automated controller for administering relevant therapies.

In certain embodiments, a decision table may be combined with computer-assisted methods to provide therapeutic guidance. In certain embodiments, a decision table may be used to select therapeutic guidance or direction.

An example is shown below. A guidance to use inotropes to increase heart strength can be made by examining the value of $E_h$, eg $E_h$<0.3. If this is not available, the guidance may be computed using SVV or PPV measures from certain cardiac output monitors.

| Condition | | Volume/Heart Guidance | SVR Guidance |
|---|---|---|---|
| MAP < MAPdes | CO < COdes | Increase Heart/Volume | Hold |
| MAP >= MAPdes | CO < COdes | Hold Heart/Volume | Decrease |
| MAP < MAPdes | CO >= COdes | Hold Heart/Volume | Increase |
| MAP >= MAPdes | CO >= COdes | Decrease Volume | Hold |

In certain embodiments of the visual representation, including but not limited to, a 2D bar chart display, recommended changes in treatment can be shown as changes to target. For example, if the current guidance is to hold the volume state, then the target volume state value can be set to the current volume state value. A similar approach can be used for other controlled variables. This can be referred to as a "dynamic targets".

Figure 4:
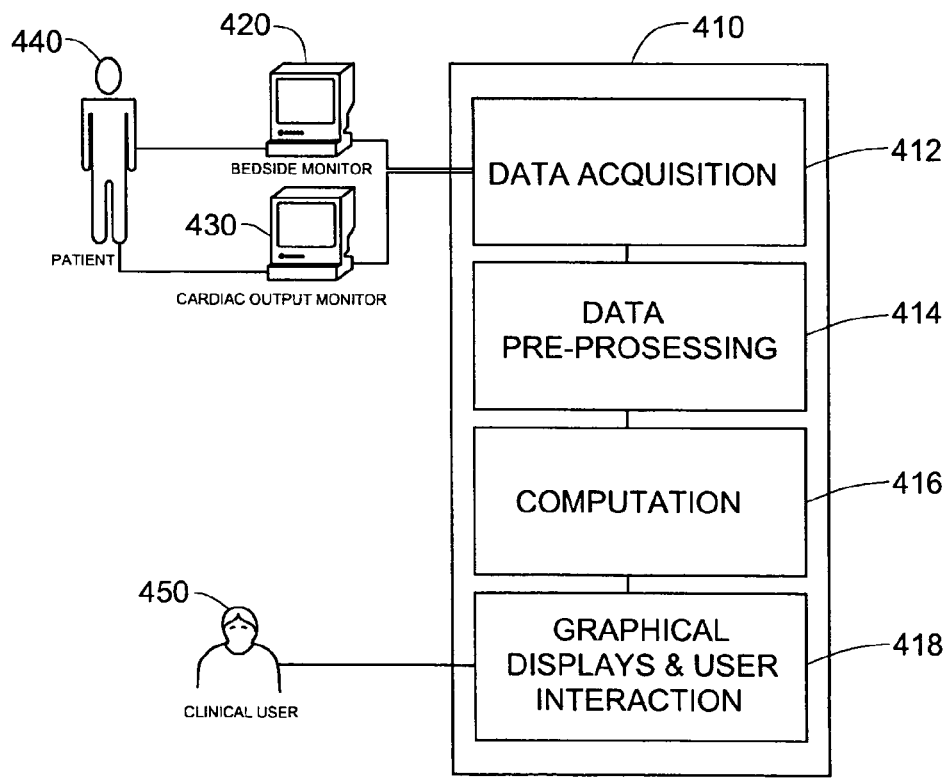
FIG. 4 is a logical block diagram of a circulatory monitoring and guidance system in accordance with certain embodiments.

FIG. 4 shows a system for circulatory monitoring and guidance in accordance with certain embodiments. The circulatory monitoring and guidance system 410 may be employed to assist clinical users in targeting, assessing and managing the circulatory system of patients in critical care. A benefit of the circulatory monitoring and guidance system 410 may include improved control of the circulatory state and reduction of side effects associated with poor control of the circulatory state.

The circulatory monitoring and guidance system 410 is shown coupled to a bedside monitor 420 and a cardiac output monitor 430. The bedside monitor 420 and cardiac output monitor 430 are coupled to a patient 440. A clinician or medical practitioner 450 may use the circulatory monitoring and guidance system 410 to monitor and control circulation of the patient 440. The circulatory monitoring and guidance system 410 may be coupled to the bedside monitor 420 and cardiac output monitor 430 via a wired or wireless interface.

The circulatory monitoring and guidance system 410 comprises a number of software modules including a data acquisition module 412, a data pre-processing module 414, a computation module 416 and a graphical display and user interaction module 418. The data acquisition module 412 communicates with the bedside monitor 420 in accordance with a defined communications protocols to request and receive data at defined rates. An example of a practical sampling rate is about once every 5 seconds. In some embodiments a 2-5 sec, 3 sec or 4 sec, rate may appropriate when the patient's cardiac output is being monitored continuously with pulse contour methods (for example on Vigileo, PiCCO or LidCO devices). This enables the user to see the immediate effect of therapy and short-term changes in the patient. When cardiac output is measured with continuous pulmonary catheter methods (e.g., Vigilance, OptiQ), sampling rates of 5 sec-5 min (e.g., 5 sec, 10 sec, 30 sec, 45 sec, 1 min, 2 min, 3 min, 4 min or 5 min) are appropriate. When cardiac output is measured intermittently (e.g., with thermodilution or ultrasound) it may be appropriate to sample cardiac output at longer times (e.g., from 5 min to 2 hours, 20 min, 1 hour, 1.5 hours, etc.). In this latter case, however, cardiac output between samples may be interpolated using pulse contour information from the arterial pulse or the oxygen saturation pulse, which enables the guidance or control system to be used continuously (a 2-5 sec time sensitivity). MAP and RAP measurements are typically available from standard bed side monitors. Cardiac output CO may be available from certain bed side monitors but may otherwise and/or obtained from a dedicated CO apparatus. The data pre-processing module 414 receives data from the data acquisition module 412 and performs range checking, artifact rejection and filtering to reduce unwanted noise signals. Suitable filters eliminate changes with, for example, sub-1 minute dynamics. Input data may be invalid for various reasons including temporary use of a catheter line for other purposes, blockage, patient lying on top of line, transducers being incorrectly leveled and so forth. When data is received, values may be inspected by algorithms to detect these events and to exclude these data points. One method to do this is to exclude values which fall out of pre-defined ranges such as 0-200 mmHg for MAP, -1-30 mmHg and less than 40% oxygen saturation and 0-20 L/min for cardiac output. Filtering following artifact rejection may be performed to reduce short-term variation or noise in the data streams. A moving average or median filter with a 95% response time of 1 min is satisfactory for blood pressure signals and continuous cardiac output signals. When cardiac output is obtained intermittently, there may be no need to filter it. Right atrial pressure signals frequently have only single digit precision. Filtering of the signals may be beneficial to provide interpolated values and smoother changes to avoid "jump" effects. There may be other methods for artifact rejection which may be used, for example, a median or other non-linear filter with a time window (e.g., 1 min, 5 min and 10 min) applied iteratively to the incoming data streams. The computation module 416 receives processed data from the data pre-processing module 414 and performs a series of computations. The graphical display and user interaction module 418 enables a user to enter patient anthropometric data, and to view the numerical values of key variables. The graphical display and user interaction module 418 displays numerical and graphical representations of the patient's circulation.

The modules described hereinbefore with reference to FIG. 4 may comprise computer software modules and may reside on an embedded computer system or a general purpose computer system such as the computer system 800 described hereinafter with reference to FIG. 8. In an alternative embodiment, the Circulatory Monitoring and Guidance System 410 may be integrated into a bedside monitor and/or cardiac output monitor. In yet another alternative embodiment, the data acquisition module 412 may be integrated into a bedside apparatus such as the bedside monitor 420 or the cardiac output monitor 430. This embodiment enables the data pre-processing module 414, the computation module 416 and/or the graphical display & user interaction module 418 to be hosted and/or executed by a computer system, such as the computer system 800 described hereinafter with reference to FIG. 8, located remotely from the patient's bedside. It will appreciate that certain of the modules described with reference to FIG. 4 may cooperate with additional electronic circuitry or hardware. For example, the data acquisition module 412 typically cooperates with an electronic circuit for sampling and processing data under software control (e.g., an analogue-to-digital converter).

Figure 5:
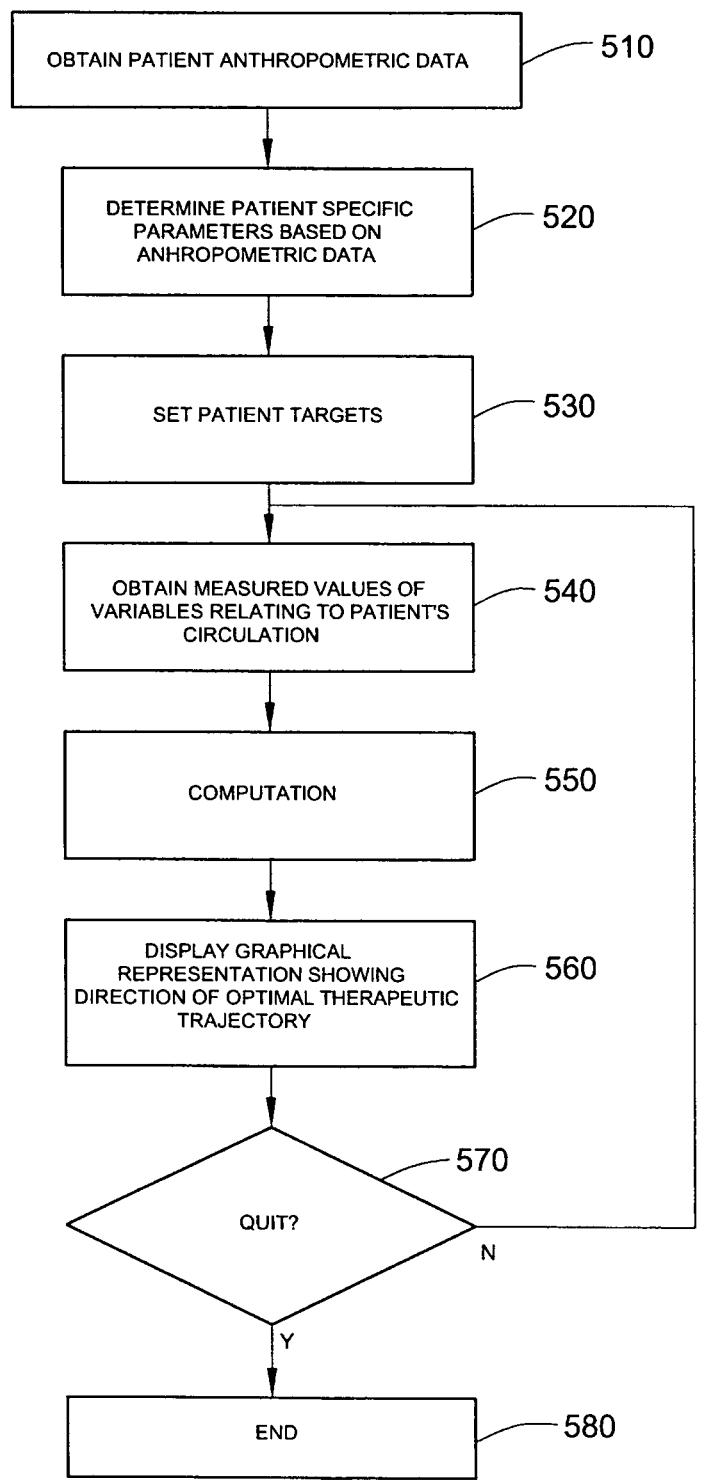
FIG. 5 is a flowchart of method for controlling a computer system for performing circulatory monitoring and guidance in accordance with certain embodiments.

FIG. 5 is a flow chart of a method implementable as a computer software program for controlling a computer system such as the Circulatory Monitoring and Guidance System 410 of FIG. 4 in accordance with certain embodiments. In step 510, a user enters patient anthropometric and other data, including age (A, years), height (H, cm), weight (W, kg), and haemoglobin (Hb). In step 520, computations are performed to determine the patient's body surface area (BSA, $m^2$), a typical cardiac index for the patient's age ($CI_{(A)}$, L/min/m²), and the corresponding cardiac output ($CO_{(A)}$ L/min). These values may be determined using equations (18)-(20), hereinafter:

$$BSA = 0.007184 H^{0.725} W^{0.425} \quad (18)$$

$$CI_{(A)} = 4.5(0.99)^{(A-15)^+} \quad (19)$$

$$CO_{(A)} = CI_{(A)} BSA \quad (20)$$

The age-adjusted norm mean arterial pressure ($MAP_{(A)}$) is:

$$MAP_{(A)} = 94.17 + 0.193 A \quad (21)$$

The coefficients a, b, c in equation 22 hereinafter are given by:

$$a = 0.96$$
$$b = 0.04$$
$$c = 0.038 \frac{MAP_{(A)}}{CO_{(A)}}$$

In step 530, the user sets desired target values for mean arterial pressure (MAP) and cardiac output (CO). It is useful in practice to be able to enter these values as upper and lower values, which define a "target zone". In step 540, actual patient data is obtained from devices such as bedside monitors and may be pre-processed as described hereinbefore. The raw data may be displayed in numeric format on the display screen. A status indicator may show whether data have been received on time, whether there are disconnections, range errors and so forth. In step 550, various derived variables are computed for the actual ("Act") patient state:

Mean systemic filling pressure:

$$P_{ms\,Act} = a RAP_{Act} + b MAP_{Act} + c CO_{Act} \quad (22)$$

Systemic vascular resistance:

$$SVR_{Act} = 80 \left( \frac{MAP_{Act} - RAP_{Act}}{CO_{Act}} \right) \quad (23)$$

In step 560, a graphical representation showing the direction of the optimal therapeutic trajectory is displayed on a display screen. The patient's position is determined by equations (27) and (28). The direction of the optimal therapeutic trajectory is determined using equations (10) to (17). In step 570, a determination is made whether the user wishes to quit. If not (N), the method reverts to step 540 for acquisition of new patient data. If the user does wish to quit (Y), the method is terminated at step 580.

Figure 6:
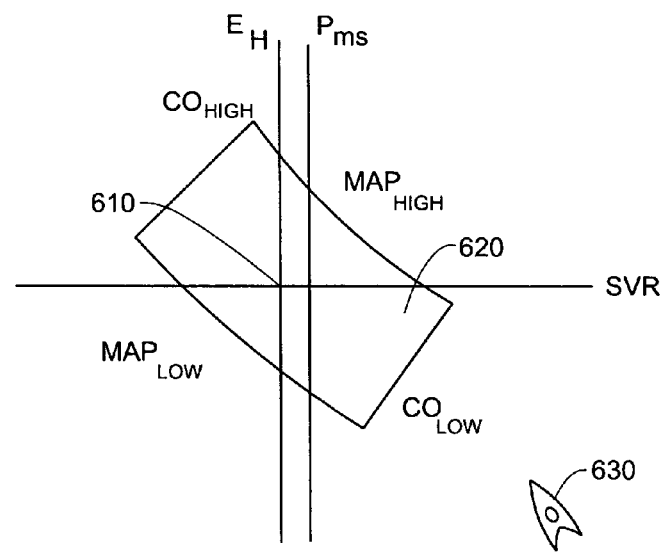
FIG. 6 is another 2-dimensional $\{P_{ms}, SVR\}$ graphical representation of the 3-dimensional $\{P_{ms}, E_H, SVR\}$ space in accordance with certain embodiments.

FIG. 6 shows an example of a graphical representation that may be practiced to perform step 560 of the method of FIG. 5 in accordance with certain embodiments. One convenient arrangement may be to position the mean target or desired patient state 610 at the centre of the graphical representation. A zone 620 representing the target range of MAP and CO for the patient may be displayed by computing and graphing the isograms corresponding to the upper and lower target values of both variables using equations (6) and (8), hereinbefore. The patient's actual position is shown as a "compass" arrow 630, which points in the direction of the optimal therapeutic trajectory. The direction of the optimal therapeutic trajectory is generally not directly towards the desired patient state 610. In practice, the graphical representation may be re-drawn with each new set of patient data. Both the axes and patient position move. An effective way is for the axes to slide on the display, giving the impression of a virtual instrument. The $E_H$ scale is plotted alongside the $P_{ms}$ scale consistent with equation (3) using the current actual value of RAP. Over time, this creates the effect of the two scales moving relative to each other. Values of $E_H$ below a threshold (e.g., 0.3) may be indicated by differently colored scale labels. If the patient's $E_H$ is low an advisory message may be generated explaining potential causes and suggesting appropriate investigations and treatment.

Figure 7:
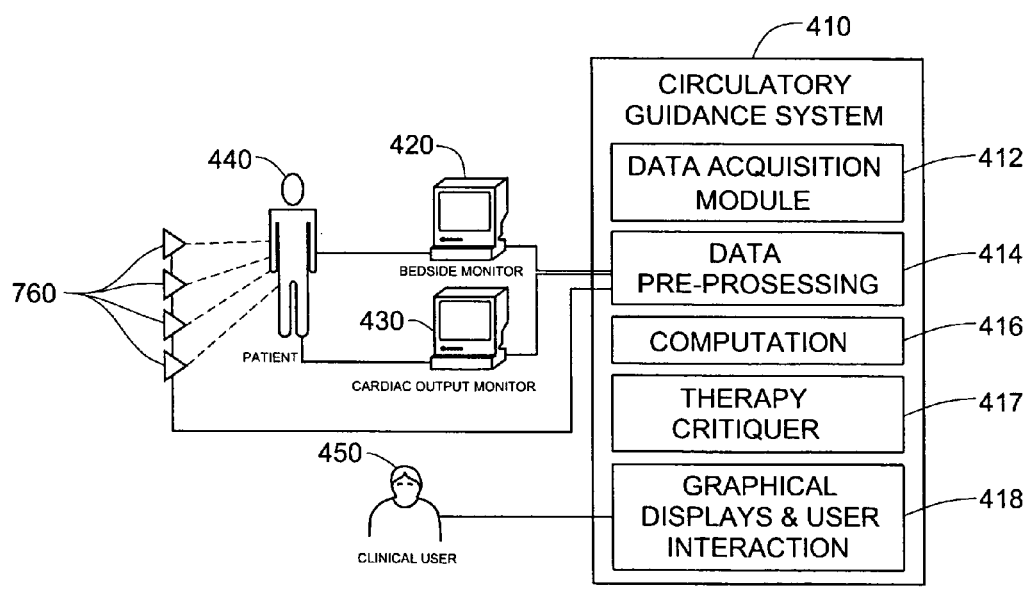
FIG. 7 is logical block diagram of another circulatory monitoring and guidance system in accordance with certain embodiments.

Certain embodiments methods and/or systems for critiquing current therapy and, if different to that advised by the circulatory monitoring and guidance system, to advise a user of this fact and of appropriate corrective action. FIG. 7 shows a block diagram of a system for critiquing current therapy that is similar to the circulatory monitoring and guidance system 410 of FIG. 4 in accordance with certain embodiments. Referring specifically to FIG. 7, the current intravenous infusion rates of volume, cardiac and vasoactive medications are acquired from the IV and/or syringe pumps 760 via the Data Acquisition Module 412. The current rates are compared with the guidance from the circulatory guidance system as described hereinbefore with reference to FIGS. 4 to 6, by the therapy critiquer module 717. If there is a variance, an explanatory warning message may be provided to a user via the display screen. Alarms or text messages may also or alternatively be generated. Certain embodiments illustrated herein (see FIG. 7) enables automatic control of circulation to be implemented by controlling the infusion rates of particular medications.

Figure 8:
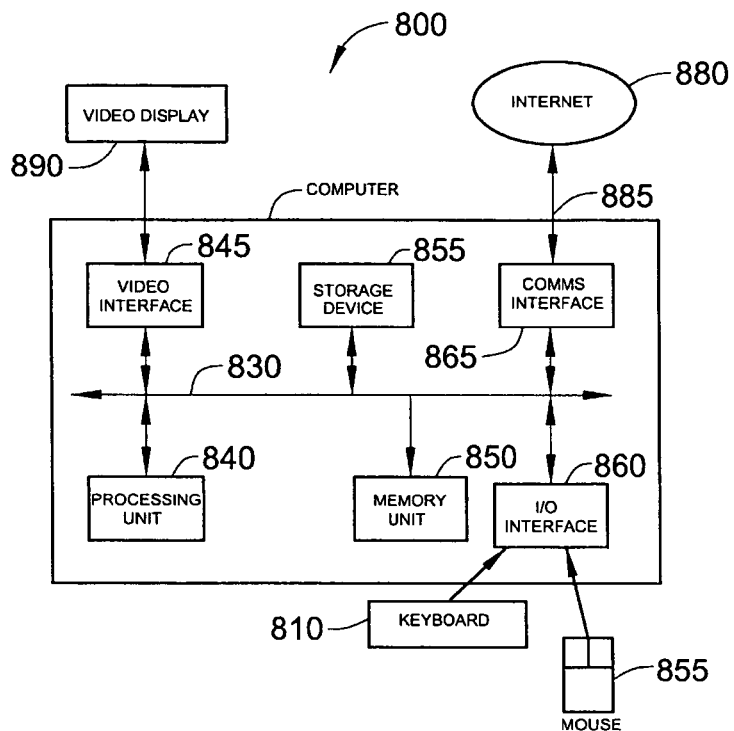
FIG. 8 is a schematic block diagram of a computer system in accordance with certain embodiments of the inventions.

FIG. 8 shows a schematic block diagram of a computer system 800 that can be used to practice the methods described herein. For example, the computer system 800 may be used to implement the Circulatory Monitoring and Guidance System 410 of FIG. 4. More specifically, the computer system 800 provides a hardware platform that may be used to execute computer software such as the computer software module described hereinbefore with reference to FIGS. 4 and 7. Accordingly, the computer system 800 may be programmed to assist in performing a method that provides therapeutic guidance for controlling a subject's circulation. The computer software executes under an operating system such as MS Windows XP™, MS Windows VISTA™ or Linux™ installed on the computer system 800.

The computer software involves a set of programmed logic instructions that may be executed by the computer system 800 for instructing the computer system 800 to perform predetermined functions specified by those instructions. The computer software may be expressed or recorded in any language, code or notation that comprises a set of instructions intended to cause a compatible information processing system to perform particular functions, either directly or after conversion to another language, code or notation.

The computer software program comprises statements in a computer language. The computer program may be processed using a compiler into a binary format suitable for execution by the operating system. The computer program is programmed in a manner that involves various software components, or code, that perform particular steps of the methods described hereinbefore. The components of the computer system 800 comprise: a computer 820, input devices 810, 815 and a video display 890. The computer 820 comprises: a processing unit 840, a memory unit 850, an input/output (I/O) interface 860, a communications interface 865, a video interface 845 and a storage device 855. The computer 820 may comprise more than one of any of the foregoing units, interfaces, and devices. The processing unit 840 may comprise one or more processors that execute the operating system and the computer software executing under the operating system. The e memory unit 850 may comprise random access memory (RAM), read-only memory (ROM), flash memory and/or any other type of memory known in the art for use under direction of the processing unit 840. The video interface 845 is connected to the video display 890 and provides video signals for display on the video display 890. User input to operate the computer 820 is provided via the input devices 810 and 815, comprising a keyboard and a mouse, respectively. The storage device 855 may comprise a magnetic or optical disk drive, or any other suitable non-volatile storage medium.

Each of the components of the computer 820 is connected to a bus 830 that comprises data, address and control buses to allow the components to communicate with each other via the bus 830.

The computer system 800 may be connected to one or more other similar computers via the communications interface 865 using a communication channel 885 to a network 880, represented as the Internet.

It will appreciate that the computer system 800 may be connected or interfaced to other external devices via the communications interface 865 or the input/output (I/O) interface 860. For example, the bedside and cardiac output monitors 420 and 430 shown in FIGS. 4 and 7 may be interfaced to the computer system 800 via the communications interface 865 (e.g., RS-232, RS-485 or Universal Serial Bus (USB)). The IV pumps 760 shown in FIG. 7 may be interfaced to the computer system 800 via the input/output (I/O) interface 860 using an analogue-to-digital converter.

The computer software program may be provided as a computer program product and recorded on a portable storage medium. In this case, the computer software program is accessible by the computer system 800 from the storage device 855. Alternatively, the computer software may be accessible directly from the network 880 by the computer 820. In either case, a user can interact with the computer system 800 using the keyboard 810 and mouse 815 to operate the programmed computer software executing on the computer 820.

The computer system 800 has been described for illustrative purposes. Accordingly, the foregoing description relates to an example of a particular type of computer system such as a personal computer (PC), which is suitable for practicing the methods and computer program products described herein. However, it will be appreciated that alternative configurations or types of computer systems may be used to practice the methods and computer program products described herein. For example, but not limited to, an embedded computer system may be used in place of the general purpose computer system 800. In such a system, the video display 890 and keyboard 810 of the computer system 800 may be integrated into the housing of the embedded computer system.

In certain embodiments, the circulatory monitoring and guidance system may be provided on a medically rated bedside touch-panel computer (e.g., Advantech POC153M or POC-S155). It may be connected to bedside physiological monitors in critical care environments. The connection from the circulatory monitoring and guidance system to the bedside physiological monitor may be via, for example, a serial cable connected to the COM 1 (RS232) or COM2 (RS422) port on the back of the computer. Cardiac output data may be obtained directly from the circulatory monitoring and guidance system or from a separate cardiac output monitor connected by serial cable to the COM 3 port. In certain embodiments, the circulatory monitoring and guidance system may automatically acquire data from the monitor(s) every five (5) seconds. Variables acquired may include mean arterial pressure (MAP mmHg), right arterial pressure (RAP mmHg), cardiac output (CO L/min) and arterial oxygen saturation (SaO$_2$%). In certain embodiments, the data may be filtered, smoothed and artifacts rejected.

The circulatory monitoring and guidance system may help clinicians set targets for the desired circulation, assess, in real time over the period of a few heartbeats, the current state of the patient's systemic circulatory state in relation to the target, and decide on appropriate treatment with reference to volume, cardioactive (inotropes and lusiotropes) and vasoactive (vasodilator and vasoconstrictor) therapies. Circulatory and heart changes take place more slowly than a few heart beats (e.g., minutes to hours) but given the severity of illness of some patients it is helpful to be able to see their circulatory state evolving with this level of time detail. Following administration of cardiac agents such as inotropes it is clinically beneficial to see how the patient is responding on this fast timescale. The guidance or control system provides great benefit when used with cardiac output methods responsive on this time interval such as PiCCO, LidCO or Vigileo.

Figure 9:
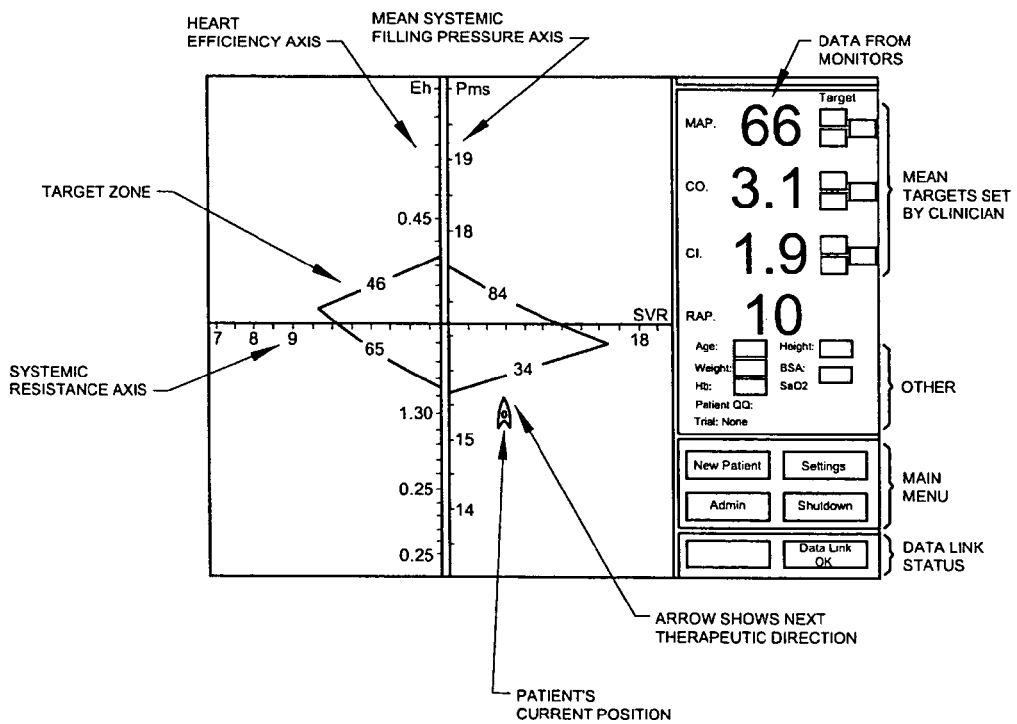
FIGS. 9-18 are an exemplary method for operating a system or device in accordance with certain embodiments.

As discussed herein, and with respect to FIG. 9, in certain embodiments, the main display of the circulatory monitoring and guidance system may show a graphical depiction of the patient's state in relation to a desired target. The mean systemic filling pressure (right hand side vertical scale) ($P_{ms}$) is a measure of volume state, or how well filled the circulation and is a prime determinant of venous return and cardiac output. The heart efficiency ($E_H \geq 0$) (left hand side of the scale) is a measure of global heart performance. It is sometimes referred to as the heart performance.

In certain embodiments, the clinician sets a target mean value for MAP and CO. The CO target mean may also be set through the corresponding cardiac index (CI). The center of the graph (where the axes cross) corresponds to the mean target MAP and CO. The "diamond" shape around the centre indicates the upper and lower limits of the desired target state.

When mean values are set for the targets, the default ranges may be set to, for example, about ±5-15% (e.g., ±5, ±7, ±9, ±10, ±11, ±13, ±14, etc.) for MAP and about ±7.5-15% (e.g., ±8, ±9, ±10, ±11, ±13, ±14, etc.) for CO and CI.

The user can identify where the patient (the solid dot in the arrow) is in relation to the desired circulation and assess the kind of intervention needed to take the patient to the target. A directional arrow on the patient symbol shows the next order of therapy. The direction is that which will take both MAP and CO closer to their target values.

The circulatory monitoring and guidance system may be applicable to critically ill patients requiring circulatory support in which MAP, RAP and CO are being monitored regularly. This includes a broad range of patients with unstable circulations presenting to the ICU critical care units, with exemplary conditions including, for example, patients aged 18 years or older, pre & post open heart surgery, pre & post major surgery, septic shock, renal failure, major burns, major trauma and cardiogenic shock.

In some embodiments, the circulatory monitoring and guidance system may require some data that is entered manually and other data that is acquired automatically from bedside devices. For example, in certain embodiments, the following anthropometric and other data items may be entered manually using the touch screen: patient initials, age (years), height (cm), weight (kg) and haemoglobin (g/L).

Additionally, in order to function, the circulatory monitoring and guidance system may use the following variables:

MAP (via direct arterial measurement or non-invasive blood pressure), cardiac output (CO) and right atrial pressure (RAP & CVP are used interchangeably).

If arterial oxygen saturation ($SaO_2$) is available, certain embodiments will use this value to calculate and display oxygen delivery index values ($DO_2I$) corresponding to the lower and upper CO range. It is important to note the accuracy of the $DO_2I$ values may depend on having a recent value of the haemoglobin.

In an exemplary embodiment, the circulatory monitoring and guidance system may launch in the manner illustrated in FIGS. 10-18.

Figure 10:
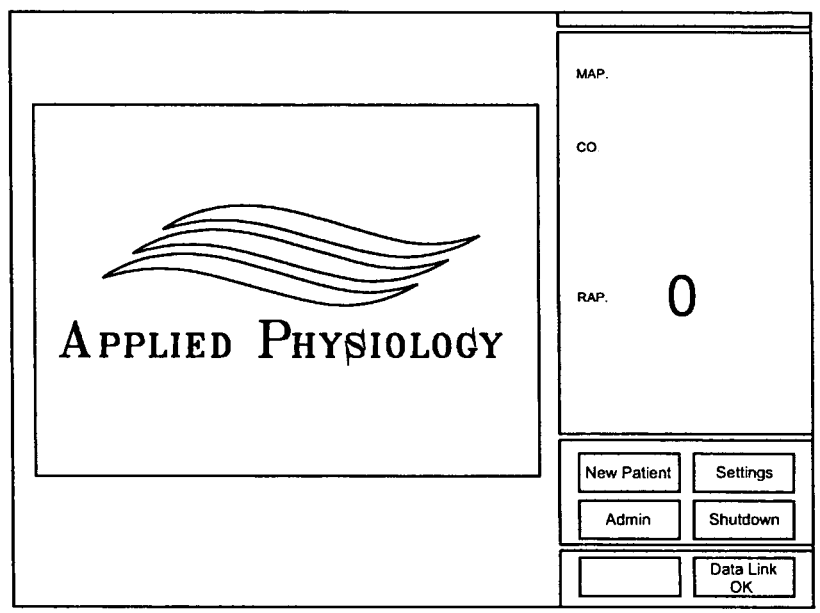
Figure 11:
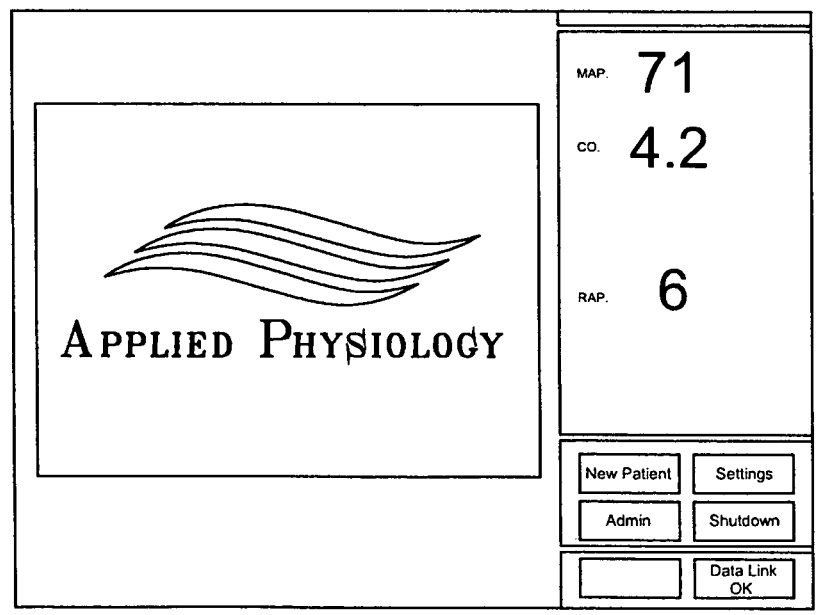
Figure 12:
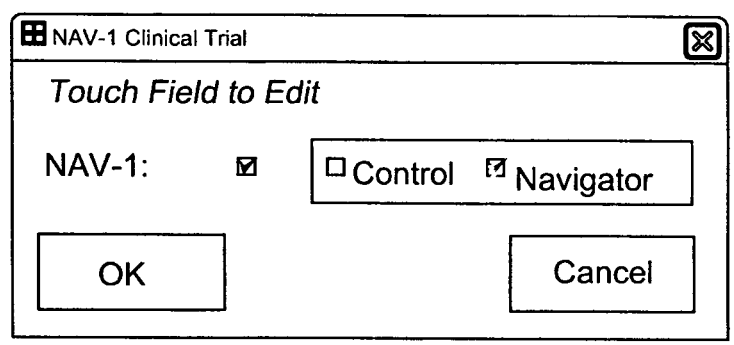
Figure 13:
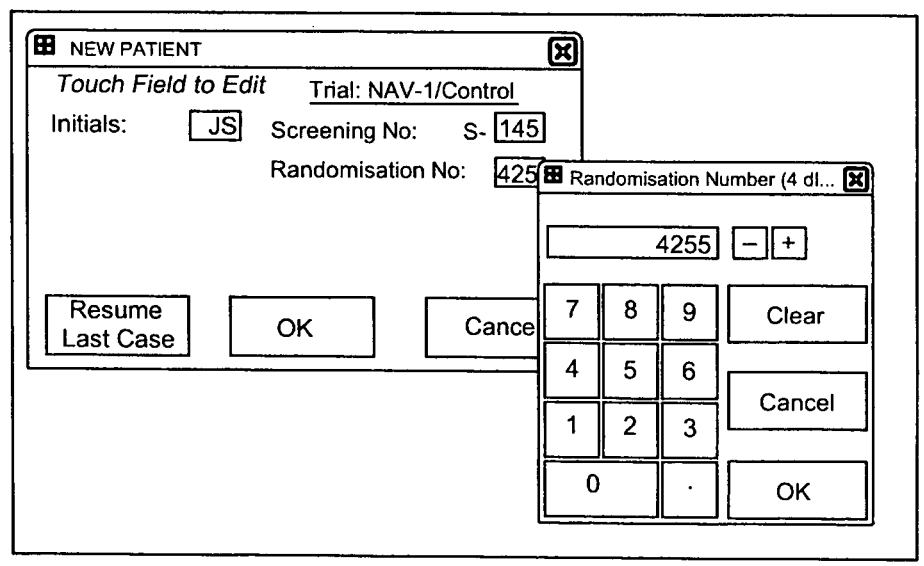
Figures 14, 15:
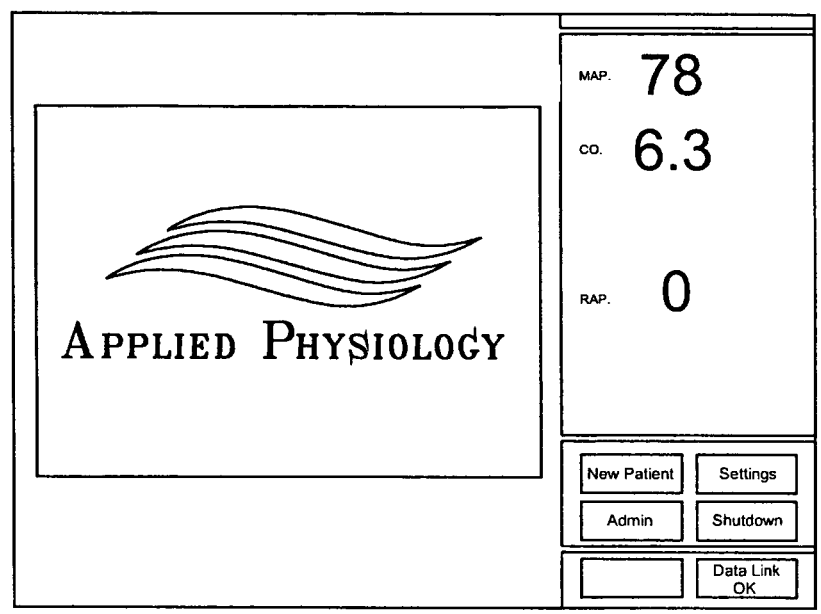

After powering on as shown in FIG. 10, the circulatory monitoring and guidance system may wait to receive data from the bedside monitor. The data link status indicator in the bottom right hand corner is set to the message "Awaiting Data". Once the data from the bedside and cardiac output monitors appears on the screen (FIG. 11), the data link status indicator typically now show the message "Data Link OK" and the user will typically confirm correlation of the values on the circulatory monitoring and guidance system with bedside monitor values. To set up the device for a new patient, the user may use a touch-sensitive screen on the device and touch the "New Patient" button in the menu area to start setting up a new patient (see FIG. 12).

Figure 16:
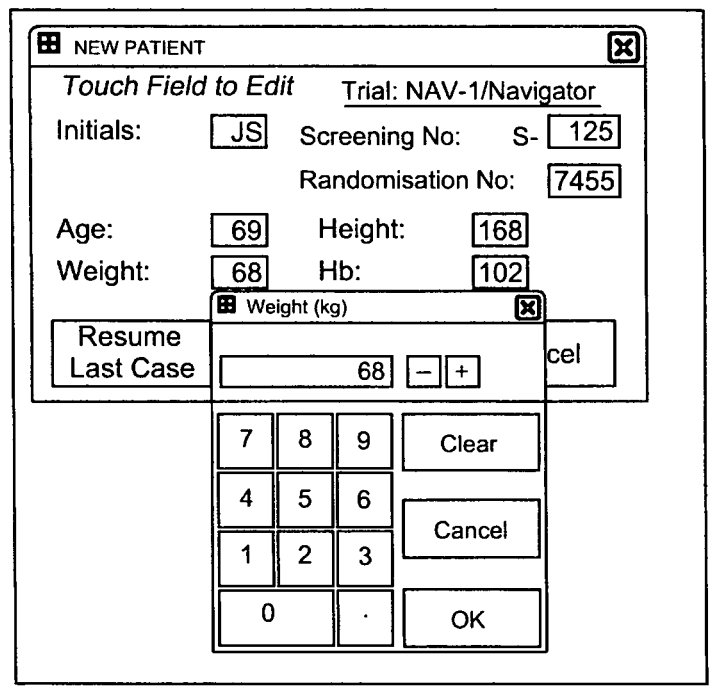

Using the Alpha numeric keypad shown in FIG. 16, the user may enter in the following information:
1. Patient Initials: First Initial First name, first initial last name.
2. Age (years)
3. Height (cm)
4. Weight (kg)
5. Haemoglobin (Hb, g/L)

In certain embodiments, the patient's height and weight may be used to calculate body surface area (BSA), which is subsequently used in calculating cardiac index (CI) therefore it may be important that these values are accurate. Once complete, the screen in FIG. 17 appears and mean target values for MAP and CO can be set by touching the field displaying the mean desired value, to the right of the two fields displaying the higher and lower values of the target range and entering the desired mean target using a pop-up keypad, for example. The initial value used is that specified at the patient randomization stage. The device will automatically set the higher and lower target ranges to, for example, ±12% of the mean for MAP and ±12% for CO or CI. (The default values of 75 mm hg for a CO of 5 liters/min may also have been set.)

Figure 17:
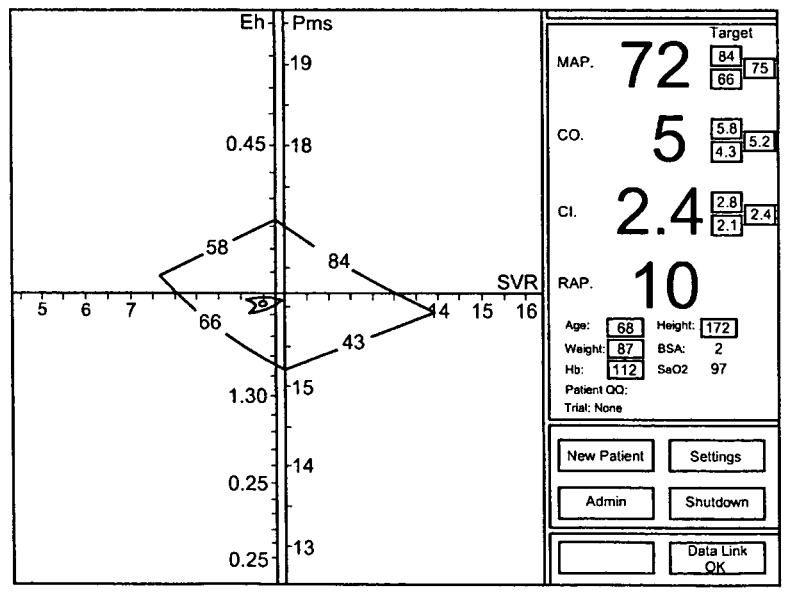

As shown in FIG. 17, CI (Norm) is the normal resting age determined CI, the value of which has been determined by using a normalized CI v Age Curve. The age dependant normal cardiac index is provided as a guide for targeting cardiac output or cardiac index with the device. The CI (Norm) may not be suitable as a target cardiac index for all patients. The CI is determined at normal body temperature (37° C.) and in the hypo- or hyperthermic patient a good rule of thumb is to reduce (hypothermia) or raise (hyperthermia) the normalized CI by 7-10% per degree C. to allow for the temperature effect.

Although the normalized resting cardiac index is a starting point, consideration may then be given to the following conditions:
1. Adequate and appropriate oxygen transport variables: these are conventional and include $DO_2$, $DO_2I$, $VO2$, mixed venous $pvO_2$, $SvO_2$, pH, lactate, etc.
2. Hydraulic variables. Some patients will require for example a higher cardiac output for purely hydraulic reasons, e.g., Fistula, recent replacement of a stenotic valve, diseases with low SVR. Setting of normal cardiac output/index targets would require undesirable vasoconstriction to maintain MAP targets.
3. The State of the patient's heart. Consideration of what the myocardium is capable of is an issue in the determination of cardiac output control targets. This relates to both upper and lower bounds. The value of $E_H$ is helpful in this regard.
4. Power Reduction. If the above three conditions are accounted for, consideration may be given to lowering cardiac output targets and reduce heart work.

Figure 18:
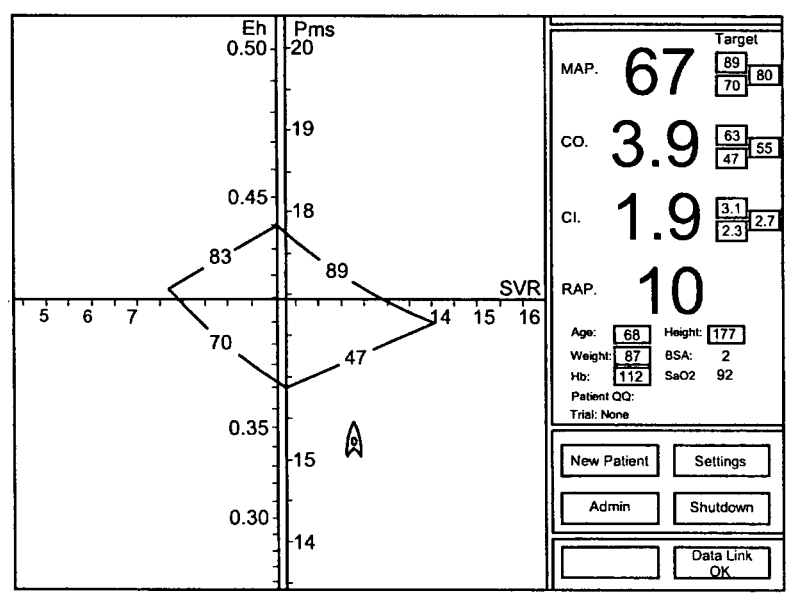

As shown in FIG. 18, on the vertical axis (to the right) is the mean systemic filling pressure ($P_{ms}$) scale, which is the measure of filling of the circulation (volume state). It is a prime determinant of venous return and cardiac output. Also displayed on the vertical axis (to the left) is the heart efficiency scale $E_H$—this is a measure of global the heart performance (efficiency). The $P_{ms}$ and $E_H$ scales are independent. On the horizontal axis is the systemic vascular resistance scale, SVR.

Referring to FIG. 18, the numeric panel on the right hand side of the display shows the data acquired from the monitors, the patient's current state is shown as a solid circle, in a arrow or "compass". The arrow indicates the next therapeutic direction. The direction of this arrow corresponds to one which takes the MAP and CO closer to their targets (based on the relationships that $P_{ms}$, $E_H$ and SVR have with MAP and CO). The scale on the y-axis where heart efficiency ($E_H$) is less than 0.3 appears with red labels. The use of inotropes may be indicated in this area.

A would be readily understood in view of the present disclosure, widespread realization of good circulation control at the bedside requires intelligent targeting and consistent continuous guidance. Adoption of such an approach relieves the clinician of the repetitive burden of the (sometimes inconsistent) task of therapeutic design. Certain embodiments disclosed herein are directed to standardization and consistency. For example, the direction of the patient "compass" symbol shows the direction of the therapeutic change that will move the patient monotonically to the target. The immediate direction may not always be towards the center. Additionally, the desired circulation will be typically continuously achieved if the patient symbol is maintained in the appropriate quadrilateral.

The vertical scale on the right through the centre shows the volume state (Pms) in mmHg and administering volume will move the patient symbol upwards; diuretics/diuresis, dialysis and venodilators will move the patient symbol downwards. The horizontal scale shows the arterial resistance (SVR) in SI units (×100). Arteriolar vasodilators (e.g. GTN, SNP) will move the patient to the left; vasoconstrictors (e.g. noradrenalin, metaraminol and/or vasopressin) will move the patient to the right.

In certain embodiments, approximately 70-80% of circulation control will be safely achieved with +/− volume and +/− arterial vasoactives. A second and independent vertical scale indicates the state of performance of the heart. The heart performance $E_H$ is given by $E_H=(Pms-RAP/P_{ms})$. The heart performance works together with the volume state to determine the vertical position of the patient (symbol) in relation to the centre target. Heart performance depends on rate, rhythm, inotropy, lusitropy in addition to mechanical impediments to the heart performance. If the heart performance $E_H \geqq 0.3$, a check of mechanical factors from "outside-in" may be performed before assuming an inotropic or lusiotropic problems exists.

Figure 19A:
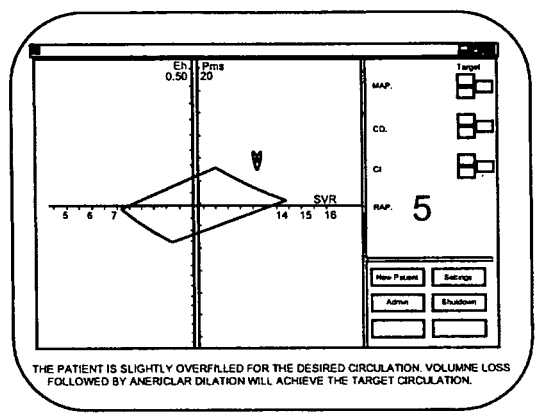
FIGS. 19a-19c are exemplary representations of the 3-dimensional $\{P_{ms}, E_H, SVR\}$ space in accordance with certain embodiments.
Figure 19B:
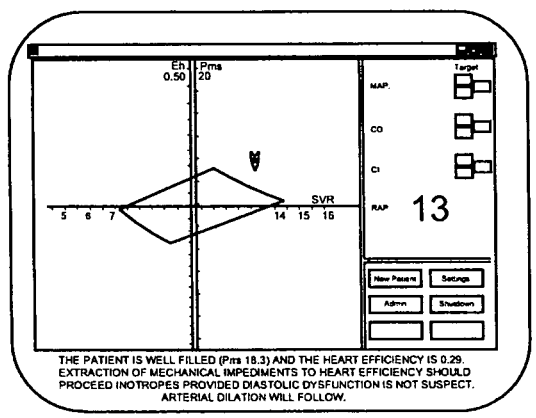
Figure 19C:
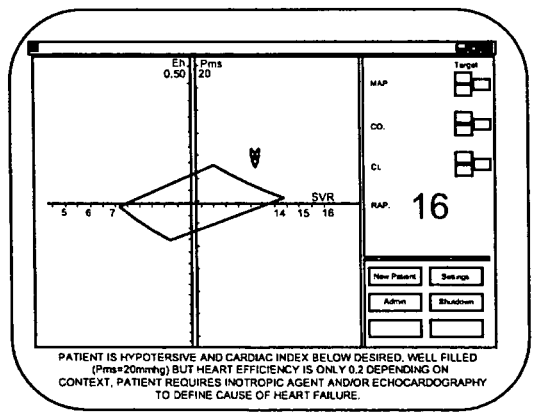

FIGS. 19a-19c illustrate various exemplary displays in accordance with certain embodiments. Specifically, FIG. 19a illustrates a display of a patient that may be slightly overfilled for the desired circulation. In this situation, volume loss, followed by arteriolar dilation may achieve the target circulation. In FIG. 19b, the patient is well filled ($P_{ms}$ is about 18.3) and the heart efficiency is 0.29. Exclusion of mechanical impediments to heart efficiency typically precede inotropes provided diastolic dysfunction is not suspect. Arterial dilation generally follows. In FIG. 19c, the patient is hypotensive and has a below desirable cardiac index. The display shows that the patient is well filled ($P_{ms}$ is about 22 mmHg) but heart efficiency is only about 0.2. Depending on context, the patient may require an inotropic agent and/or echocardiography to help define the cause of the heart failure.

In certain embodiments, the $P_{ms}$ measurement may be used to control venous return rather than the cardiac output as discussed above. This process helps define the volume state of the systemic circulation. Unlike a typical preload measure, $P_{ms}$ has no dependence upon the heart or circulatory resistances. Measuring $P_{ms}$ opens the possibility of closed loop servo control of the volume state, e.g., in dialysis. $P_{ms}$ further enables the measurement of $E_H$ which, as discussed above, defines the operation of the global heart and may be used as the object of servo control for cardioactive agents. As detailed below, some of the value of $E_H$ is volume recruitable if the patient is "volume responsive"—the remainder depends upon intrinsic properties of the heart and factors in the thorax local to the heart.

The notion of "volume responsiveness" has evolved over time because it has been progressively realized that measures of the absolute value of preload (whichever is chosen) are poor or non-predictors of dynamic (MAP, CO etc) response to volume therapy.

Volume responsiveness is typically predicted by measuring systolic pressure variation, pulse pressure or pulse volume variation in patients on positive pressure ventilation. As the intrathoracic pressure rises and RAP rises the venous return (and CO) fall (discussed in more detail below). This effect may be ablated at higher values of $P_{ms}$. Measurement of $P_{ms}$ and Eh enables a quantitative approach to volume responsiveness. The maximum possible volume responsiveness may be calculated and the actual response measurable as a percent of the maximum. This may be a further use for $P_{ms}$ in the quantitation of circulation definition and response to therapy. Therefore, in certain embodiments, by using $P_{ms}$, measured circulatory variables may be resolved into their volumetric, resistive and cardiac parts. (e.g., $P_{ms}$ may be used in a range of derivatives for circulation control).

Generally, at a simple clinical level, the assessment of volume state calls upon historical information (e.g., a history of fluid loss such as vomiting or diarrhoea) and the observation and assessment of a group of signs (e.g., increased heart rate, low blood pressure, low pulse volume, low venous pressure, low urine output, diminished sensorium, etc). Together, the history and examination may detect major volume state disturbances. Where more sophisticated measurements are available, measures of the "preload" of the heart have historically formed a major part of the appreciation of the volume state. This is based on Starling's Law of the Heart (discussed above). These are direct or derived pressure or volume measures of the state of filling of the ventricles of the heart during diastole. They include measures such as the right atrial pressure (RAP), right and left end diastolic ventricular pressures and volumes (RVEDP, LVEDP, RVEDV, LDEDV) together with many other signals. Although preload may be defined in numerous ways, it is clear that preload measures have resistance and heart determinants, in addition to volume determinants but are not true volume measures.

Low blood pressure and flow will result from a heart that does not contract vigorously (inotropic disorder). A similar clinical picture will result from a heart that contracts well but relaxes poorly during diastole. In this case the heart will not fill and there will therefore be less blood to pump in the following systole (lusitropic disorder). This disorder is sometimes called diastolic dysfunction.

Bedside distinction of these two different states can be difficult. Inotropic problems are treated with an inotropic drug which increases the vigour of systolic contraction of the heart (e.g., adrenaline). Lusitropic disorders are treated by filling the heart to a higher volume state, i.e., they are "volume responsive" (see below). They may also be treated with drugs.

As discussed above, $P_{ms}$ is the steady state pressure in the circulation when the heart is stopped. In many mammals, including humans, this static pressure is normally about 7 mmHg. $P_{ms}$ may be measured using, for example, formula (I) above. $P_{ms}$, which may normally be controlled by the kidney together with water and sodium intake, is a major determinant of the venous return to the heart. Starling's Law ensures that the cardiac output is servo controlled to the systemic venous return $VR_S$, $$VR_s = \frac{P_{ms} - RAP}{RVR} \qquad (24)$$

where RVR is resistance to venous return, determined significantly by tissue oxygen flow and metabolites together with neural and endocrine control.

As also discussed above, variable $E_H$ is an extremely useful measure of the global performance state of the heart, determined in turn by rate, rhythm, inotropy, lusitropy, etc. The systemic vascular resistance (SVR) is a measure of the relationship between blood pressure and flow (cardiac output) analogous to Ohm's Law and may be defined as, $$SVR = \frac{MAP - RAP}{CO} \qquad (25)$$

As discussed above, the new derived measures of $P_{ms}$ and $E_H$ together with the systemic vascular resistance (SVR) may be combined to continually display the position of the patient in relation to the three prime therapeutic dimensions, the volume, resistance and heart states and other variables, such as oxygen delivery and venous oxygen in various graphical realizations. This instrument allows the targeting of a desired mean arterial pressure range and cardiac output or oxygen delivery range, which together define a control target area. As discussed earlier, in certain embodiments the horizontal axis of this instrument may have one scale, the systemic vascular resistance scale (SVR) and the vertical axis may have two scales on the y-dimension, the $P_{ms}$ scale and the $E_H$ scale. This is because, although the circulation control problem is three-dimensional, increase in both $P_{ms}$ and $E_H$ increase MAP and CO. The $2^{nd}$ vertical scale $E_H$ can be plotted next to $P_{ms}$ for the current RAP given equation (3). In an exemplary device, the patient's position may be shown as a solid circle enclosed in an arrow (or "compass"). This arrow shows the preferred next direction of therapy needed to achieve the target circulation. There are other 2-D and 3-D visual graphical representations that may be used as discussed above.

A practical clinical issue is not infrequently whether to increase MAP and/or CO by giving more fluid and increasing $P_{ms}$ (with the attendant risk of oedema and especially pulmonary oedema) or to start an inotropic or chronotropic drug like adrenaline which, in increasing the force and rate of the heart will increase $E_H$, MAP and CO. Neither approach is without risk.

In contemplation of giving volume and increasing $P_{ms}$, one may be interested to know in advance whether the patient is "volume responsive", i.e., whether MAP and CO will increase significantly for a small rise in $P_{ms}$ or the contrary. $P_{ms}$ increases with administration of volume.

Consideration of equation (1) shows that an increase of $P_{ms}$ could be variously partitioned between RAP, MAP and CO. This partitioning depends on how effectively the heart is beating and the circulatory resistances. Note that it is both MAP and CO that are of interest here. If RAP increased alone, but without change in MAP or CO, no additional power output would be achieved and the patient would thus not be "volume responsive".

If MAP or CO or both increase, then more power is being delivered and patient is volume responsive. We are thus interested in the power output W delivered by the heart to the circulation. Accordingly, it is the power responsiveness that is of interest in volume responsiveness (e.g., changes in response to changes of $P_{ms}$). W may be given by:

$$W = CO(MAP - RAP) \quad (26)$$

Through mathematical derivation, W may be expressed in terms of $P_{ms}$, $$W = \frac{P_{ms}^2 E_H^2 SVR}{RVR^2} \quad (27)$$

Volume responsiveness (α) may be measured as the sensitivity of W to $P_{ms}$ changes, i.e., the partial derivative, $$\alpha = \frac{\partial W}{\partial P_{ms}} = \frac{2W}{(P_{ms} - RAP)}\left(1 - \frac{\partial RAP}{\partial P_{ms}}\right) \quad (28)$$

This expression for α allows appreciation of the anticipated power rise (mmHg·L/min) when the volume state ($P_{ms}$) is increased by 1 mmHg, i.e., the volume responsiveness. The maximum volume responsiveness, at the current operating position, may be given by:

$$\alpha_{Max} = \frac{2W}{(P_{ms} - RAP)} \quad (29)$$

The actual volume responsiveness (α) can be indexed ($\alpha_I$) by division by the patient's body surface area, or normalized by division by its maximum value ($\alpha_N$). In the latter case, $$\alpha_N = \frac{\alpha}{\alpha_{Max}} = \left(1 - \frac{\partial RAP}{\partial P_{ms}}\right) \quad (30)$$

Volume responsiveness may diminish with volume administration, for example when RAP and $P_{ms}$ increase faster than MAP and CO. If volume responsiveness is low but increases with volume administration, this may indicate that the heart exhibits a lusitropic disorder.

The measures of volume responsiveness may be variously incorporated into instruments or systems for circulatory guidance and control.

The principles laid out above may be applied to manufacturing a software based device to assist in circulatory care in mammalian patients. The device may be similar to the device described above with respect to FIG. 4. As discussed above, the purpose of the Circulatory Guidance System is to assist clinical users in targeting, assessing and managing the circulatory system of patients in critical care. It does this by acquiring data in real time from bedside monitors, allowing the user to enter other patient parameters and desired or target circulatory values, computing derived variables and displaying these in a visual control chart. The benefit of the system is the improved control of the circulatory state and reduction of side effects associated with poor control.

The circulatory guidance system interfaces to the bedside monitor and cardiac output monitor through standard physical connections serial or networked, wired or wireless. The Data Acquisition Module communicates with the bedside device according to their specific and published communications protocols to request and receive data at defined rates. A practical sampling rate is about 5 seconds. Typically measurements of MAP and RAP are available from the standard beside monitor. Cardiac output CO is sometimes available from the bedside monitor and sometimes from dedicated devices. The Data Pre-Processing Module receives raw data from the Data Acquisition Module and performs range checking, artifact rejection and filtering to reduce signal noise. The Computation of Derived Variables module performs a series of computations based on the principles. These are outlined in more detail below.

The Graphical Display and User Interaction Module allow the user to enter anthropometric and target data, and to see the numerical values of key variables. It displays a graphical chart showing the patient's actual and desired state on $P_{ms}$, SVR axes and also showing a dynamic $E_H$ axis alongside the $P_{ms}$ axis. The optimal tactical trajectory is shown as an arrow.

The various software modules can reside on the same hardware, running a general purpose or embedded operating system. A flexible arrangement is for the Data Acquisition Module to be a server and for it to communicate with the other modules using IP protocols and XML. This enables the Data Acquisition Module to be deployed on separate hardware as a dedicated unit deployed close to the bedside monitors.

Figure 20:
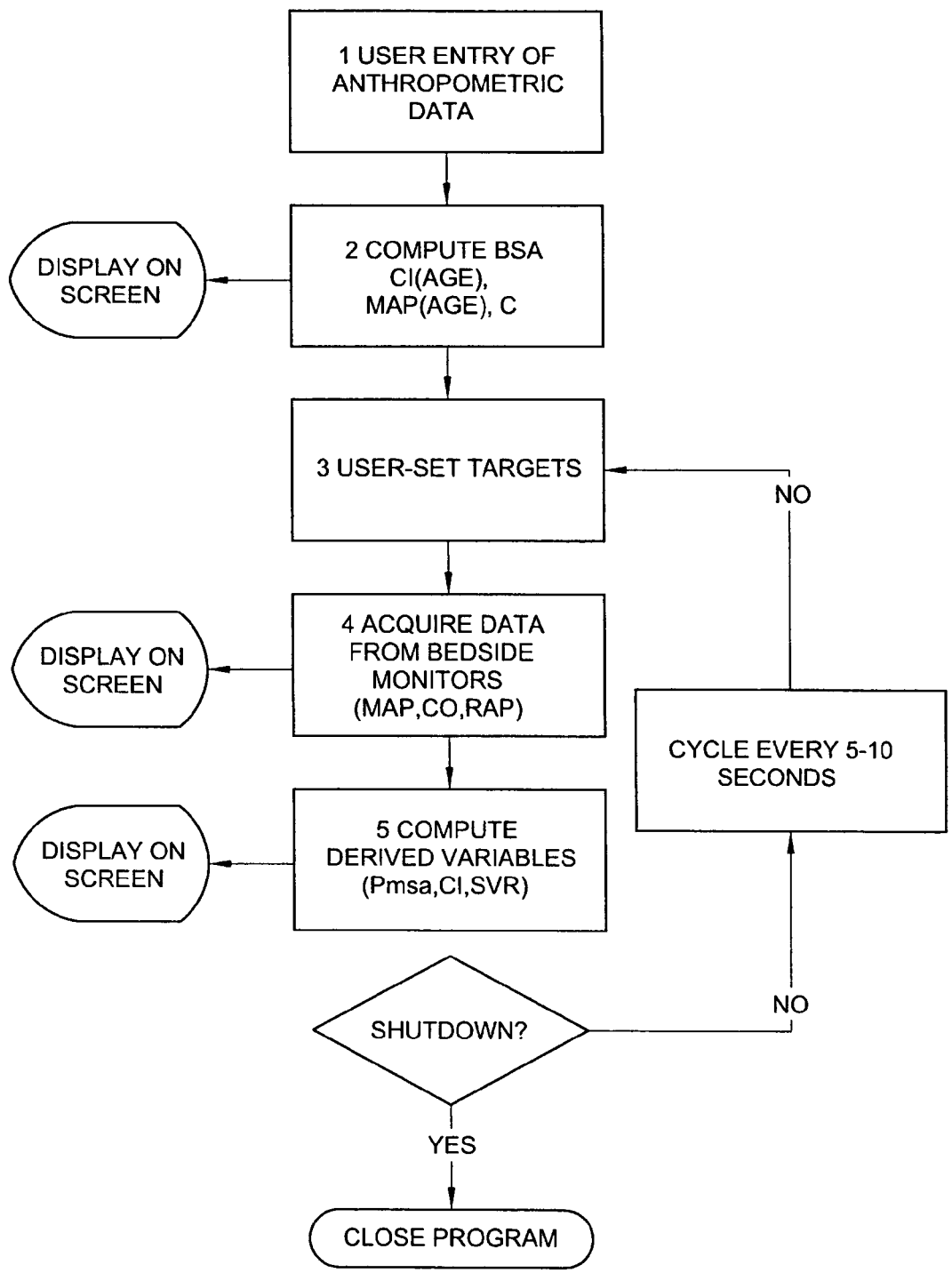
FIG. 20 is an exemplary algorithm for controlling a circulatory guidance system in accordance with certain embodiments.

FIG. 20 shows the main elements of the software algorithm that controls the Circulatory Guidance System. In Step 1, the user can enter anthropometric and other data required by the algorithms, including age (A, years), height (H, cm) and weight (W, kg). In Step 2, computations are made of body surface area (BSA, m²), the typical cardiac index for the patient's age ($CI_{(A)}$, L/min/m²) and the corresponding cardiac output ($CO_{(A)}$L/min) as in equations (18)-(20) above. The age-adjusted norm mean arterial pressure ($MAP_{(A)}$) is determined by equation (21) avoce and the coefficients may be the same as described with respect to Equation (21). In Step 3, the user can set the desired target values for mean arterial pressure (MAP) and cardiac output (CO). It is useful in practice to be able to enter these values as upper and lower values, which contain a "target zone". In Step 4, data are requested and received from the connected devices via the Data Acquisition Module. At this step, the data are pre-processed as described above. The raw data may be displayed in numeric format on the display screen. A status indicator can show whether data have been received on time, whether there are disconnections, range errors and so forth. In Step 5, various derived variables are computed for the actual patient state (denoted by "Act"), namely the mean systemic filling pressure and systemic vascular resistance as defined by equations (22) and (23) above.

Note that these are best computed using the filtered or smoothed values of raw data after artifact rejection.

A chart in the form of FIG. 1 is displayed on the display screen. The patient's position is defined by equations (22) and (23). The direction of the optimal therapeutic trajectory is displayed as an arrow and computed using methods previously described. A zone representing the target range for MAP and CO is displayed by computing and graphing the isograms corresponding to the upper and lower target values of both variables using methods previously described. A convenient arrangement of the graphical chart is to position the mean target at the centre of the chart.

In practice, the chart is re-drawn with each new data receipt. Both the axes and patient position move. An effective way is for the axes to slide on the display, giving the impression of a virtual instrument. The $E_H$ scale is plotted alongside the $P_{ms}$ scale consistent with equation (3) using the current actual value of RAP. Over time, this creates the effect of the 2 scales moving relative to each other. Values of $E_H$ below a threshold (usually 0.3) may be indicated by differently colored scale labels. If the patient's $E_H$ is low an advisory message may be generated explaining potential causes and suggesting appropriate investigations and treatment.

The current volume responsiveness index of the patient's circulation may be computed using, $$\alpha_{Act} = \frac{2W_{Act}}{(P_{msAct} - RAP_{Act})}\left(1 - \frac{\partial RAP}{\partial P_{ms}}\bigg|_{Act}\right) \quad (31)$$

$W_{Act}$ may be computed using $$W_{Act} = (MAP_{Act} - RAP_{Act})CO_{Act} \quad (32)$$

In equation (31) an estimate needs to be made of $\delta RAP/\delta P_{ms}$. A method to do this is as follows: observe and record $P_{ms}$ and RAP over a period of minutes (typically 5-8 min). Test for a systemic rise (or fall) of $P_{ms}$ over the period of a minimum amount (typically 1-2 mmHg)–$\Delta P_{ms}$. If there has been a systemic rise of $P_{ms}$, the retrieve the corresponding change in RAP-$\Delta$RAP. Estimate $\delta RAP/\delta P_{ms}$ as $\Delta RAP/\Delta P_{ms}$.

In the presence of significant noise it is advisable to apply a further filter to the $P_{ms}$ and RAP data. Typically a median filter with a 5 min. window is suitable.

Figure 21:
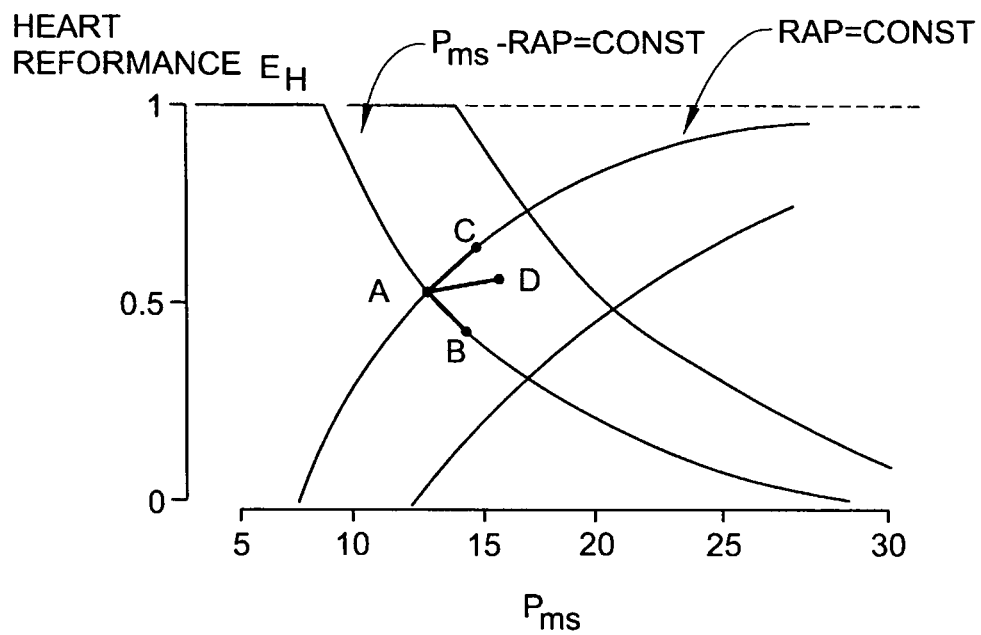
FIG. 21 is an exemplary relational chart for $E_H$ versus $P_{ms}$ in accordance with certain embodiments.
Figure 22:
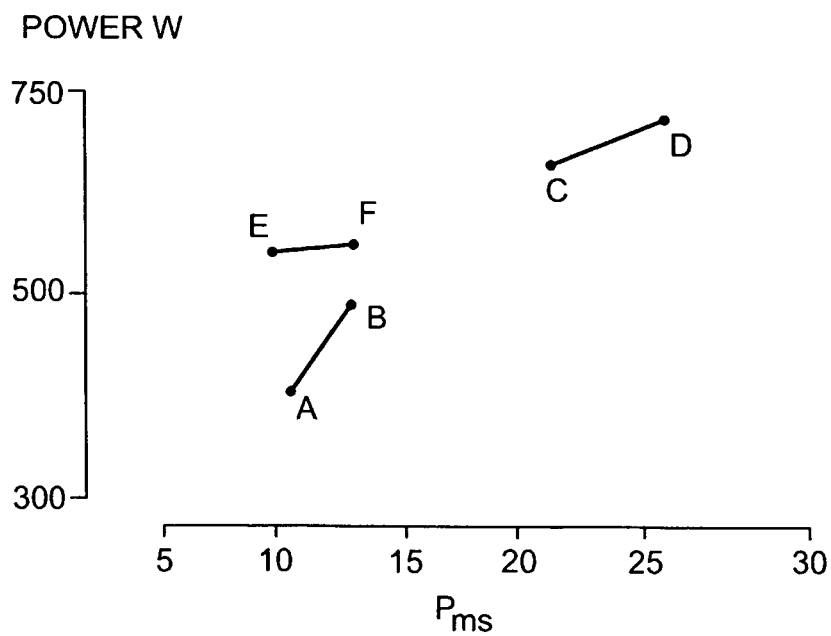
FIG. 22 is an exemplary relational chart for W versus $P_{ms}$ in accordance with certain embodiments.

There are a variety of methods to output the volume responsiveness results. The choice of variables is threefold, and in some circumstances it is helpful to have all three: Absolute volume responsiveness $\alpha_{Act}$; Volume responsiveness indexed by body surface area $\alpha_I = \alpha_{Act}/BSA$; and Volume responsiveness normalized by the maximum possible volume responsiveness at the current operating point $\alpha_N = \alpha_{Act}/\alpha_{Max}$. These results may be displayed as labeled numeric fields or as graphical charts. There are a range of possible graphical charts including:

1. On a 1-dimensional scale—this helps visualize the current value in relation to reference points (such as $\alpha_{Max}$);
2. As time series—this is useful in showing trends;
3. A relational chart of heart performance $E_H$ versus mean systemic filling pressure $P_{ms}$. An example of such a chart is depicted in FIG. 21. Over time, the patient's position moves as a trajectory over this chart. Consider a patient at A. If they move to point B, then the increase in $P_{ms}$ is directed to RAP, and the patient has zero volume responsiveness. Point C is on the constant RAP line and corresponds to maximum volume responsiveness. Point D is the general case where the slope of the line AD corresponds to tan θ as described above; and
4. A relational chart of power W versus mean systemic filling pressure $P_{ms}$. An example of such a chart is depicted in FIG. 22. Over time, the patient's position moves as a trajectory over this chart. The slope of the trajectory is the current value of the patient's absolute volume responsiveness $\alpha_{Act}$. Consider a patient at A moving to point B with a particular slope and $\alpha_{Act}$. Sometime later they move from C to D with a lesser slope. This is analogous to the Starling curve, where increase of heart output reduces as driving pressure increases. An innovation is the ability to trace a Starling type response for a patient. This is enabled by using mean systemic pressure. Another patient at E has a similar mean systemic pressure to the patient at A. However, this patient does not respond with the same slope, and is much less volume responsive.

Below, various volume responsiveness scenarios and general examples of certain embodiments will be described.

Zero Volume Responsiveness

In the case that there is zero volume responsiveness, $P_{ms}$–RAP=const, and $$\left(1 - \frac{\partial RAP}{\partial P_{ms}}\right) = 0 \Rightarrow \alpha = 0 \quad (33)$$

Conceptually, in this case, the change in volume state $P_{ms}$ is reflected in RAP change. None of the increased volume state changes CO or MAP.

In the case of $E_H$ being constant with $P_{ms}$ changes:

$$\frac{\partial RAP}{\partial P_{ms}} = \frac{RAP}{P_{ms}} \quad (34)$$

In this case the volume responsiveness becomes $$\alpha = \frac{2W}{P_{ms}} \quad (35)$$

For Maximal Volume Responsiveness, a patient can be said to be "maximally volume responsive" when the volume state $P_{ms}$ change goes to CO or MAP change, and none to RAP change. The heart is capable of delivering the added volume state into pressure or flow. In this case, $$\frac{\partial RAP}{\partial P_{ms}} = 0 \text{ and; hence} \quad (36)$$

$$\alpha_{Max} = \frac{2W}{(P_{ms} - RAP)} \quad (37)$$

Volume responsiveness may be indexed to the patient's body surface area ($\alpha_I = \alpha/BSA$) or to the maximal volume responsiveness ($\alpha_N = \alpha/\alpha_{Max}$). In the latter case, it follows that $$\alpha_N = \frac{\alpha}{\alpha_{Max}} = \left(1 - \frac{\partial RAP}{\partial P_{ms}}\right) \quad (38)$$

In a practical system, it is useful to compute and display $E_H$ and to observe how it changes with $P_{ms}$. The local slope is defined as:

$$\tan\theta = \frac{\Delta E_H}{\Delta P_{ms}} \quad (39)$$

This may be easier to estimate than $\delta RAP/\delta P_{ma}$, which is more sensitive to measurement noise. The general form (A12) becomes"

$$\alpha = \frac{2W}{(P_{ms} - RAP)}\left[1 - \left(\frac{RAP}{P_{ms}} - P_{ms}\tan\theta\right)\right] \quad (40)$$

As discussed above, in determining the target cardiac output (CO), the clinician may use values chosen from experience or based on the patient's age, height, weight and metabolic state. However, in certain embodiments, if the arterial oxygen saturation $S_aO_2$ is known (e.g., from an oximeter finger clip) and arterial oxygen content is calculated, such as based on the following equation:

$$C_aO_2 = Hb \times 1.34 \times S_aO_2 \quad (41)$$

The oxygen delivery =(CO×$C_aO_2$) or oxygen delivery index=CI×$C_aO_2$ may be displayed for the target CO and used to target the required CO.

Alternately, if the $S_aO_2$, $S_vO_2$ and CO are known, the CO target to achieve a certain $\dot{V}O_2$, ($S_vO_{2desired}$) may be determined based on the following equation:

$$\dot{V}O_2 = CO(C_aO_2 - C_vO_2) \quad (42)$$

and assuming in the first instance that the $\dot{V}O_2$ remains constant, the cardiac output required to achieve an $S_vO_{2desired}$ may be given by:

$$CO_{desired} = \frac{\dot{V}O_2}{(C_aO_2 - C_vO_{2desired})} \quad (43)$$

In certain embodiments, as CO increases, this approach may be used iteratively to attain the desired CO for a target $S_vO_2$.

More specifically, the venous oxygen ($S_vO_2$) is a measure of the oxygen "left over" after the body has consumed ($\dot{V}O_2$, oxygen consumption) what has been delivered (CO.$C_aO_2$, oxygen delivery). A low $S_vO_2$ generally calls for a higher cardiac output. This may assist monitor described herein with cardiac output targeting by "forward estimating" the cardiac output for a particular $S_vO_2$, $C_vO_2$, a form of targeting.

The $S_{cv}O_2$ can be measured using right atrial catheters and is different in value typically from the mixed venous saturation $S_{mv}O_2$ measured using fibre optic pulmonary artery catheters. Both signals are generally continuous and may be measured using the Vigileo ($S_{cv}O_2$), and Vigilance ($S_{mv}O_2$). The venous oxygen is a measure of the balance between oxygen delivery $DO_2$=CO($C_aO_2$) and oxygen consumption $\dot{V}O_2$=CO($C_aO_2$—$C_vO_2$).

Measuring the venous oxygen is a mainstay of the oxygen economy allowing assessment of the sensitivity of the oxygen consumption to changes in oxygen delivery. Especially, one can assess if oxygen consumption is supply dependent, enabling better assessment of the wisdom of increasing cardiac output as a strategy to improve tissue oxygenation.

Measurement of $S_vO_2$ ($S_{cv}O_2$ or $S_{mv}O_2$) without knowledge of $\dot{V}O_2$ may, in certain embodiments, be misleading in situations of disordered circulation (e.g. sepsis) where regional maldistribution of flow may decrease $\dot{V}O_2$ and increase $S_vO_2$. When $S_vO_2$ is measured one should know the cardiac output and $S_aO_2$. In the absence of such knowledge, outcome may be improved in sepsis by manipulating cardiac output on the basis of the $S_{cv}O_2$.

In certain embodiments, the place of $S_vO_2$($S_{cv}O_2$, $S_{mv}O_2$) in circulation control may be consolidated by integrating $S_aO_2$ and $S_vO_2$ data into the determination of the target cardiac output. Knowledge of CO and $S_aO_2$, $C_aO_2$ may be used to measure oxygen delivery and the CO increase required to attain a desired $DO_2$ or $DO_2I$. Knowledge of CO, $C_aO_2$, $C_vO_2$ enables estimation of $\dot{V}O_2$ using equations (41) and (42).

Assuming that $\dot{V}O_2$ remains constant the CO increase required to achieve a target $S_vO_{2desired}/C_vO_{2desired}$ may be calculated using equation (43).

Certain embodiments may produce the following exemplary results.

Example 1

An 18 year old female patient, 2 days after fixation of thoraco-lumbar spine, and with a history of vomiting, with copious quantities of bright red blood. On examination, she was mentally obtunded, extremely pale, anxious, had a heart rate of 180. Her peripheral circulation was very shutdown and she was sweating. The most likely diagnosis is a gastric ulcer or Mallory-Weiss tear.

Figure 23:
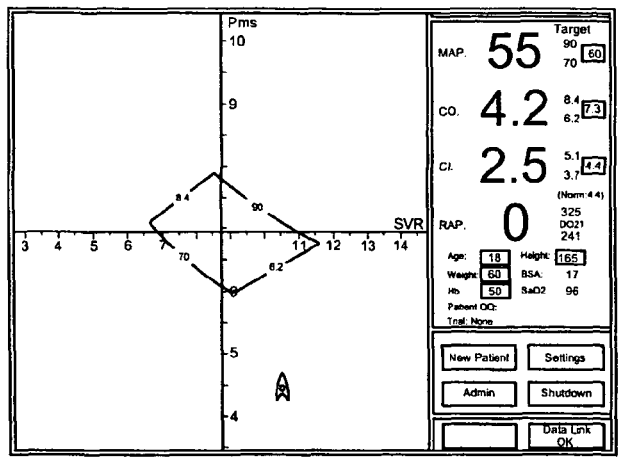
FIGS. 23-29 are exemplary representations of the 3-dimensional $\{P_{ms}, E_H, SVR\}$ space in accordance with certain examples provided herein.

The initial solution is shown in FIG. 23 which shows a low cardiac output and blood pressure in the setting of a very low mean systemic filling pressure ($P_{ms}$). The normal value of $P_{ms}$ is 7 mmHg. This is the pattern of profound hypovolemia. Sometimes the mean arterial pressure (MAP) is better preserved in young people than is the case here.

Example 2

Figure 24:
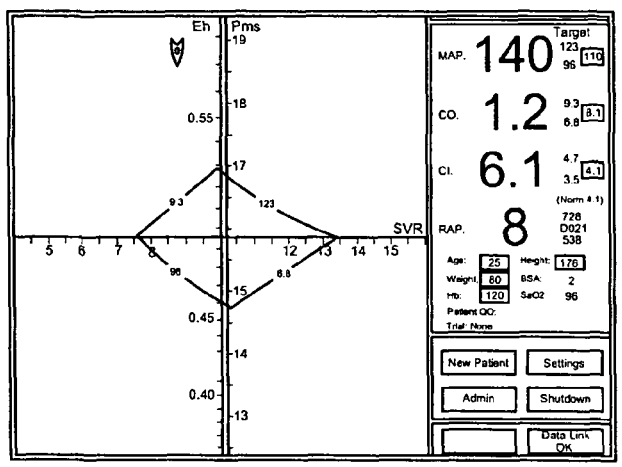
Figure 25:
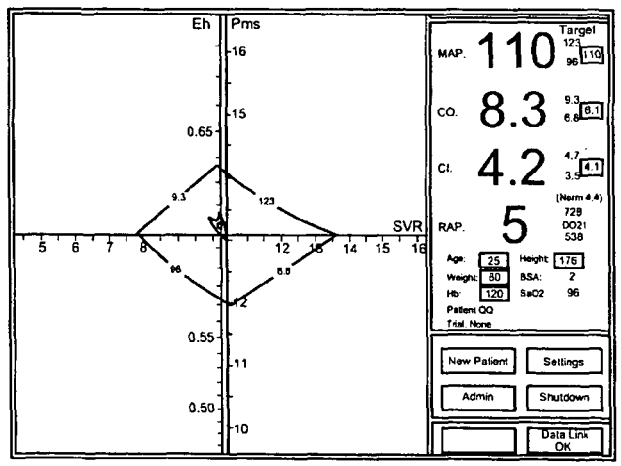

A 25 year old female patient that is prima gravida (first child), 26 weeks pregnant. She has a history of hypertension of pregnancy. Admitted to hospital at 22 weeks and placed on a range of anti-hypertensive therapies. The therapy failed to control the hypertension. She was admitted to the ICU after 4 weeks in the obstetric unit for the control of hypertension with sodium nitroprusside as a prelude to delivery of a 26 week pregnancy. The screen shot in FIG. 24 reveals that both mean arterial pressure and cardiac output are abnormally high, even for pregnancy. The $P_{ms}$ of 19 mmHg suggests strongly that the hypertension was secondary to being over-filled. The patient was treated with diuretics, had an excellent diuresis and the mean blood pressure fell to 110 mmHg and the cardiac output to 8.3 L/min (see, FIG. 25). No delivery was necessary to control hypertension.

Example 3

Figure 26:
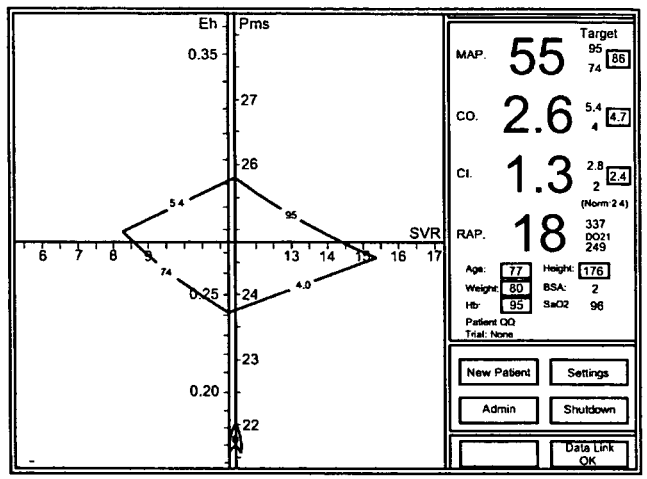

The patient is an 82 year old male, who had elective open heart surgery. Two hours post-operatively the patient became hypotensive and the measured cardiac index fell to 1.3 L/min/m². The right atrial pressure rose to 18 mmHg. On the screen shot illustrated in FIG. 26, the $P_{ms}$ rose to 22 mmHg and the heart performance $E_H$ fell to 0.17.

In such a situation, mechanical causes of heart failure may be considered. In this patient, the right atrial pressure and pulmonary artery mean pressure became equal, meaning that the right ventricle was no longer doing the required work. A pericardial tamponade was relieved with urgent thoracotomy and the patient did well. When $E_H \leq 0.25$ it is often a good idea to do a trans thoracic echocardiograph.

Example 4

Figure 27:
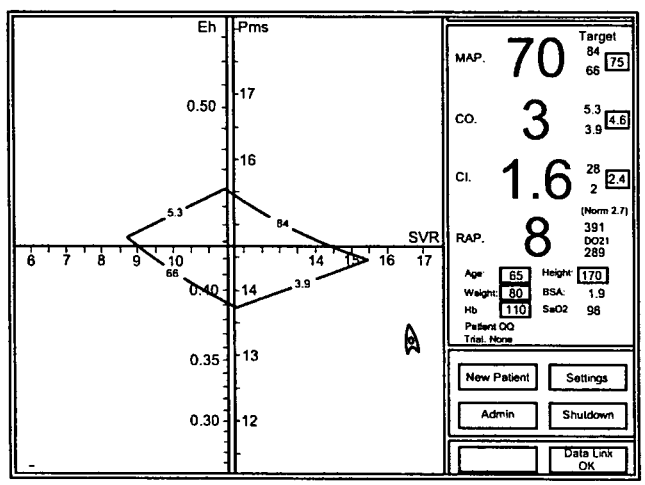
Figure 28:
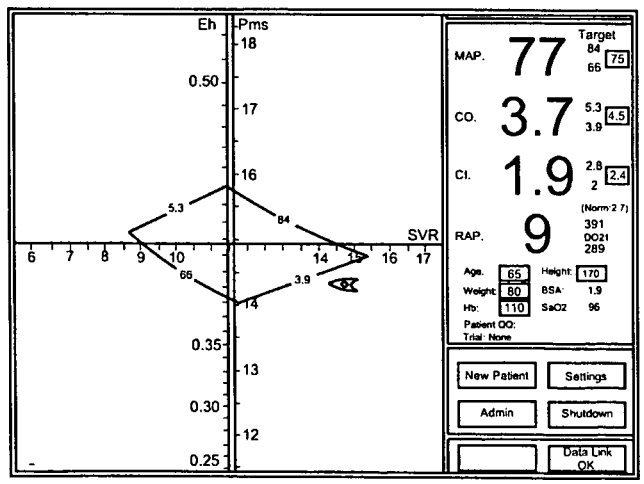
Figure 29:
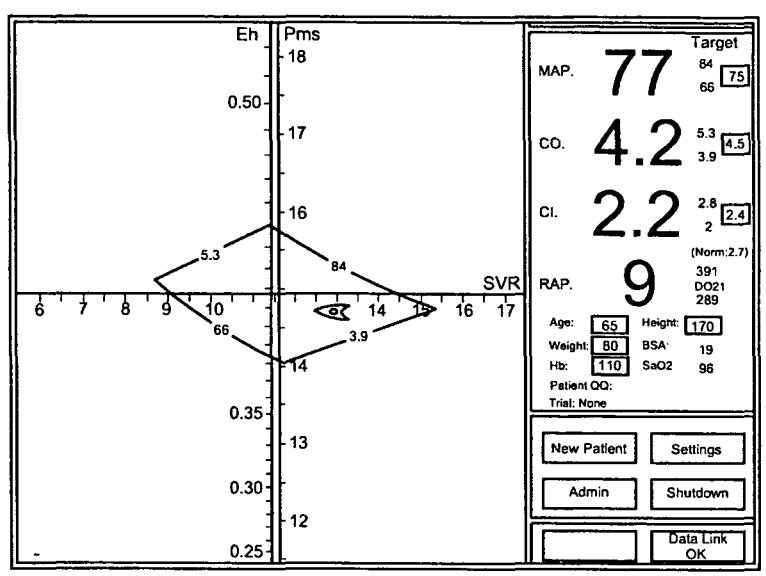

The patient is a 65 year old woman following emergency aortic aneurysm repair. There was a history of pre-operative abdominal pain and distension. The patient was anuric. Laparotomy revealed a ruptured infra-renal aortic aneurysm. The screen in FIG. 27 shows the patient's situation on return to the ICU. The patient is both hypovolemic and arterially vasoconstricted. The patient compass is suggesting fluid therapy before the institution of vasodilators. The next screen (FIG. 28) shows the situation following the administration of volume therapy. The mean systemic pressure ($P_{ms}$), mean arterial pressure (MAP) and cardiac output (CO) have all risen. The compass now suggests that the patient be arterially dilated in order to improve the cardiac index and oxygen delivery so that the patient may be within the target region as shown in FIG. 29.

Certain embodiments of methods, systems, devices and computer program products are disclosed that provide, among other things, therapeutic guidance for controlling a subject's circulation. Certain embodiments enable a clinician or medical practitioner to monitor circulation in a patient and advantageously assist in therapeutic maintenance of subject circulatory dynamics. Embodiments of the present inventions are applicable to mammalian subjects other than human beings, including, but not limited to, domestic animals such as dogs, cats and horses. The coefficients in certain of the equations described hereinbefore may be changed to reflect different sizes, and age-adjusted normal values in different animals.

Example 5

A study was conducted to evaluate the safety and efficacy of a guidance system in accordance with certain embodiments. The study's objective was to demonstrate that the use of this guidance system safely provides the clinician with appropriate data and guidance to better achieve and maintain tighter haemodynamic stability when compared to conventional care. Haemodynamic stability was measured by a patient's closeness to a target mean arterial pressure (MAP) and cardiac output or index (CO, CI) as prescribed by the physician. A target region around the targets was defined by upper and lower boundaries. This study was a multi-centre, prospective, randomized controlled trial conducted in 7 Australian tertiary ICUs. The patient population comprised 112 patients recovering in ICU following surgery consisting of coronary bypass grafting and/or heart valve repair or replacement, using cardio-pulmonary bypass.

Method:

The version of Navigator™ used was a free-standing touch-panel monitor that integrates with bedside multi-parameter and hemodynamic monitors. The Navigator™ version used in this study continuously acquires data from the bedside monitors every few seconds. The data includes mean arterial pressure (MAP), right atrial pressure (RAP), cardiac output and index (CO, CI) and arterial and venous oxygen saturations (SaO2, SvO2). Other data such as patient age, height, weight and hemoglobin are manually entered into the system by the user. The physician specifies the prescribed circulation (the "target" circulation) by entering mean values or ranges for MAP, CO or CI and/or oxygen delivery index (ODI). The Navigator computes estimates of mean systemic filling pressure (Pms—a measure of volume state), heart performance (Eh) and a conventional measure of systemic vascular resistance (SVR). The patient's current state and target state are charted on a display, which shows the therapeutic change needed to take the patient into the target zone. The axes of the display correspond to volume (or diuretic), vasoactive and cardioactive therapies. A guidance arrow advises on next appropriate therapy. The display is updated every few seconds and provides 24 h continuous support to the bedside nurse and physician, as the patient's state changes in response to disease process or therapy. The goals of hemodynamic therapy are specified for the clinical team, as well as progress in achieving them. Patients were randomized to Navigator-supported clinician care or to conventional clinician care on admission to the ICU. Although data on MAP and CO were continuously logged in both arms only those patients randomized to the treatment (Navigator) arm had the benefit of the Navigator graphical interface showing continually the patient position in relation to the targets set. In the control arm the Navigator graphical display was blacked out. The primary endpoint was a measure of how well both MAP and CO were stabilized to the centre of this target region, whilst connected to Navigator. The average standardized distance or ASD in this study was defined as follows: the 2 variables being controlled, MAP and CO, were combined in a normed Euclidean distance measure, scaled by the respective widths of their target regions. This is referred to as the "average standardized distance" or ASD.

Number of Subjects:

According to the protocol sufficient patients were to be consented to allow 100 patients to complete the study (50 in each treatment arm). A total of 112 patients were enrolled into the study and formed the intent to treat population. Of these 105 patients completed the study as planned and formed the modified intent to treat (MITT) population (57 patients in the Navigator™ arm and 48 patients in the control arm). Patient demographics (see Table 1), enrolment status (see Table 2) and surgical procedures (see Table 3) were matched between the Navigator and control arms.

TABLE 1

Summary of Subject Demography

| | | NAV-1 (N = 59) | Control (N = 53) | Total (N = 112) |
|---|---|---|---|---|
| AGE (YEARS) | N | 59 | 53 | 112 |
| | MEAN (SD) | 61 (12) | 67 (11) | 64 (12) |
| | MEDIAN | 63 | 67 | 64 |
| | MIN, MAX | 31, 85 | 45, 90 | 31, 90 |
| SEX | MALE | 45 (76.3) | 35 (66.0) | 80 (71.4) |
| | FEMALE | 14 (23.7) | 18 (34.0) | 32 (28.6) |
| RACE | CAUCASIAN | 38 (64.4) | 38 (71.7) | 76 (67.9) |
| | ASIAN | 3 (5.1) | 0 (0.0) | 3 (2.7) |

TABLE 1-continued

Summary of Subject Demography

|  |  | NAV-1<br>(N = 59) | Control<br>(N = 53) | Total<br>(N = 112) |
|---|---|---|---|---|
|  | AFRICAN-AMERICAN | 1 (1.7) | 0 (0.0) | 1 (0.9) |
|  | HISPANIC | 0 (0.0) | 1 (1.9) | 1 (0.9) |
|  | OTHER | 8 (13.6) | 6 (11.3) | 14 (12.5) |
|  | NOT COLLECTED | 9 (15.3) | 8 (15.1) | 17 (15.2) |
| HEIGHT<br>(CM) | N | 59 | 53 | 112 |
|  | MEAN (SD) | 170.57 (8.975) | 167.19 (8.961) | 168.97 (9.088) |
|  | MEDIAN | 170.00 | 168.00 | 169.50 |
|  | MIN, MAX | 150.0, 189.0 | 149.0, 188.0 | 149.0, 189.0 |
| WEIGHT<br>(KG) | N | 59 | 53 | 112 |
|  | MEAN (SD) | 85.32 (17.986) | 79.60 (16.219) | 82.61 (17.335) |
|  | MEDIAN | 84.60 | 79.40 | 82.30 |
|  | MIN, MAX | 53.0, 140.0 | 40.6, 120.6 | 40.6, 140.0 |

TABLE 2

Summary of Enrolment, Status and Disposition

|  | NAV-1<br>(N = 59) | Control<br>(N = 53) | Total<br>(N = 112) |
|---|---|---|---|
| INTENT-TO-TREAT POPULATION | 59 (100.0) | 53 (100.0) | 112 (100.0) |
| COMPLETED STUDY AS PLANNED | 57 (96.6) | 50 (94.3) | 107 (95.5) |
| WITHDREW FROM STUDY | 2 (3.4) | 3 (5.7) | 5 (4.5) |
| REASONS FOR WITHDRAWAL: |  |  |  |
| ADVERSE EVENT | 1 (1.7) | 0 (0.0) | 1 (0.9) |
| PATIENT NON-COMPLIANCE | 0 (0.0) | 0 (0.0) | 0 (0.0) |
| PATIENT REQUEST | 0 (0.0) | 0 (0.0) | 0 (0.0) |
| INVESTIGATOR OR SPONSOR REQUEST | 0 (0.0) | 0 (0.0) | 0 (0.0) |
| TERMINATION OF THE STUDY BY THE SPONSOR | 0 (0.0) | 0 (0.0) | 0 (0.0) |
| PROTOCOL VIOLATION | 0 (0.0) | 1 (1.9) | 1 (0.9) |
| THE PATIENT DIED | 1 (1.7) | 0 (0.0) | 1 (0.9) |
| LOST TO FOLLOW-UP | 0 (0.0) | 0 (0.0) | 0 (0.0) |
| OTHER | 0 (0.0) | 2 (3.8) | 2 (1.8) |

TABLE 3

Summary of Baseline Characteristics

|  |  | NAV-1<br>(N = 59) | Control<br>(N = 53) | Total<br>(N = 112) |
|---|---|---|---|---|
| TYPE OF SURGERY: |  |  |  |  |
| CORONARY ARTERY BYPASS GRAFTING |  | 46 (78.0) | 42 (79.2) | 88 (78.6) |
| VALVULAR REPAIR |  | 2 (3.4) | 3 (5.7) | 5 (4.5) |
| MITRAL VALVE |  | 5 (8.5) | 3 (5.7) | 8 (7.1) |
| PROSTHESIS INSERTED: RING |  | 0 (0.0) | 2 (3.8) | 2 (1.8) |
| PROSTHESIS INSERTED: VALVE |  | 13 (22.0) | 13 (24.5) | 26 (23.2) |
| VALVULAR REPLACEMENT |  | 14 (23.7) | 13 (24.5) | 27 (24.1) |
| AORTIC VALVE |  | 14 (23.7) | 18 (34.0) | 32 (28.6) |
| OTHER |  | 2 (3.4) | 3 (5.7) | 5 (4.5) |
| DURATION OF SURGERY (MINS) | N | 58 | 52 | 110 |
|  | MEAN (SD) | 263 (74) | 243 (74) | 254 (75) |
|  | MEDIAN | 255 | 230 | 248 |
|  | MIN, MAX | 115, 420 | 135, 526 | 115, 526 |

TABLE 3-continued

Summary of Baseline Characteristics

| | | NAV-1 (N = 59) | Control (N = 53) | Total (N = 112) |
|---|---|---|---|---|
| DURATION ON NAVIGATOR (HOURS) | N | 59 | 51 | 110 |
| | MEAN (SD) | 26.19 (19.255) | 20.16 (13.890) | 23.39 (17.174) |
| | MEDIAN | 20.09 | 18.56 | 19.70 |
| | MIN, MAX | 0.4, 116.4 | 0.1, 76.6 | 0.1, 116.4 |
| DURATION IN ICU (HOURS) | N | 57 | 45 | 102 |
| | MEAN (SD) | 53.01 (30.742) | 51.20 (30.052) | 52.21 (30.303) |
| | MEDIAN | 46.50 | 45.07 | 46.13 |
| | MIN, MAX | 18.2, 160.3 | 12.8, 146.5 | 12.8, 160.3 |
| DURATION IN HOSPITAL (HOURS) | N | 52 | 47 | 99 |
| | MEAN (SD) | 217.72 (126.683) | 258.91 (205.500) | 237.28 (169.120) |
| | MEDIAN | 173.32 | 188.67 | 177.42 |
| | MIN, MAX | 116.3, 702.1 | 117.0, 1012.0 | 116.3, 1012.0 |

Figure 37:
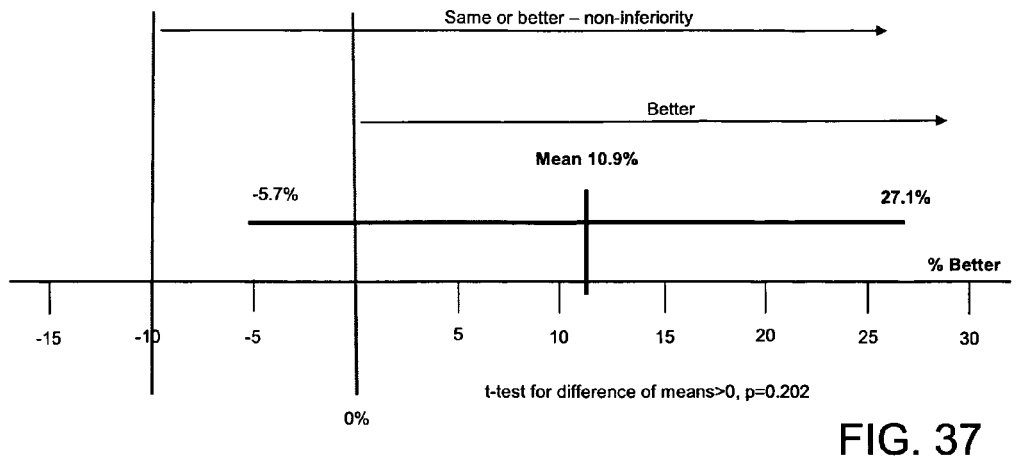
FIG. 37 is an exemplary illustration of primary endpoint results.

Primary Endpoint Results:

The ASD in Navigator patients was 1.71 vs. Control 1.92, for all patients, all centres and all time connected to Navigator. The lesser value represents improved haemodynamic stability with Navigator, —a benefit of 10.9% (see FIG. 37). The t-test of difference in means gave a p-value of 0.202 with the 95% CI of the difference, −5.7% worse to 27.1% better for Navigator compared to control. Note that ASD is the average control over the entire period for which the Navigator was connected.

We concluded that a Navigator-supported clinician achieves haemodynamic stability with the same or better performance than an unsupported clinician (non-inferiority conclusion). There was a strong trend towards superiority for Navigator. The ASD measure does not have an intuitive interpretation. Further, there is an "area" effect—the area enclosed by the ASD is proportional to the square of the ASD, yet we compared the radial changes.

Figure 38:
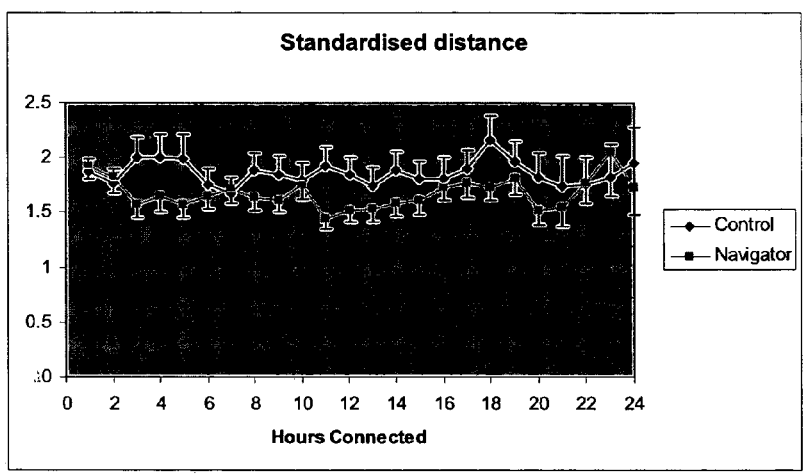
FIGS. 38-39 are charts comparing certain data results.
Figure 39:
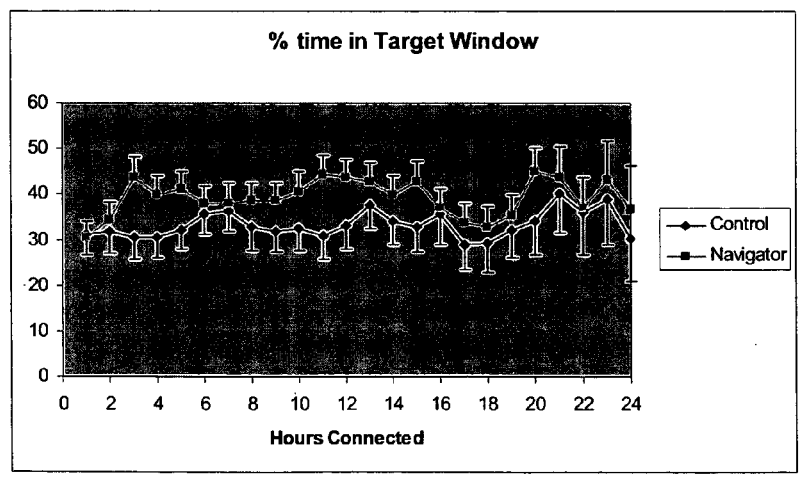

The secondary endpoint of time in target zone is easier to understand and interpret clinically. There was an increase in percentage of time in the target zone from control 32.4% to Navigator 38.4% (p=0.116), an absolute increase of 6.0% with 95% confidence interval −1.5% decrease to a 13.5% increase. The absolute increase of 6% corresponds to a relative increase of 18.5%. The benefit judged this way is substantially greater than with ASD. The ASD and % time in target zone were also analyzed for each 1 hour block of care, as shown in FIGS. 38 and 39.

By the third hour after ICU admission, Navigator patients were in the target zone 44% of the time, compared with 30% in the control group (p=0.047). Navigator patients were maintained better at target levels. Over the subsequent 8 hours of care, Navigator patients were in target 40% of the time, and control patients 33% of the time. Post hoc analysis showed that there was a significant effect of ICU centre on mean ASD. There was greater heterogeneity than anticipated in both control levels and Navigator effect amongst centres. For example, the control level of ASD varied from 1.26 to 2.44 between centres. We examined this effect with ANOVA using treatment arm and centre as variables. ANOVAs were performed on ASD and % time in target zone over the first 12 hours of care. There is a trend significance in the treatment effect for both ASD and % time in target zone (see Table 4 below).

TABLE 4

| | Source | Type II Sum of Squares | df | Mean Least Squares | F Value | Sig. |
|---|---|---|---|---|---|---|
| % time in window | Treat | 14753.563 | 1 | 14753.56 | 3.461 | 0.066 |
| | Centre | 79869.904 | 5 | 15973.98 | 3.757 | 0.004 |
| Std Dist. | Treat | 18.245 | 1 | 18.245 | 3.248 | 0.075 |
| | Centre | 129.556 | 5 | 25.911 | 4.625 | 0.001 |

Secondary Efficacy Endpoints:

There was an increase in percentage of time in the target zone from control 32.4% to Navigator 38.4% (p=0.116), over all patients and centres (not correcting for centre control heterogeneity). Incidence of AF whilst connected to Navigator was low, (Navigator 5.3%, Control 6.3%) and not significantly different. SOFA scores were not statistically significantly different between the two treatment arms on Day 1 and Day 2. There was a statistically significant difference between the two treatment arms in terms of mean SOFA scores in favour of Navigator at Day 3. There were no serious adverse events classified as associated with Navigator. There were no device failures.

Other Results:

Total fluid intake, urine output and blood loss were similar between both groups (Table 5). Table 6 shows a summary of patients who received one or more treatments with inotropes and vasoactives.

TABLE 5

Summary of Fluid Balance

| | | NAV-1 (N = 59) | Control (N = 53) | Total (N = 112) |
|---|---|---|---|---|
| TOTAL FLUID INTAKE FOR THE TIME ON NAVIGATOR (ml) | N | 58 | 50 | 108 |
| | MEAN (SD) | 4868.09 (3241.93) | 4523.80 (2224.57) | 4708.69 (2809.77) |
| | MEDIAN | 4131.00 | 4088.00 | 4088.00 |
| | MIN, MAX | 723.0, 19996.0 | 916.0, 10955.0 | 723.0, 19996.0 |
| TOTAL URINE OUTPUT FOR THE TIME ON NAVIGATOR (ml) | N | 58 | 50 | 108 |
| | MEAN (SD) | 2707.50 (1810.01) | 2428.08 (1405.96) | 2578.14 (1634.03) |
| | MEDIAN | 2436.50 | 2052.50 | 2197.00 |
| | MIN, MAX | 15.0, 12030.0 | 420.0, 6402.0 | 15.0, 12030.0 |
| TOTAL BLOOD LOSS FOR THE TIME ON NAVIGATOR (ml) | N | 56 | 49 | 105 |
| | MEAN (SD) | 600.21 (368.468) | 597.37 (388.604) | 598.89 (376.166) |
| | MEDIAN | 510.00 | 475.00 | 500.00 |
| | MIN, MAX | 120.0, 2500.0 | 74.0, 2348.0 | 74.0, 2500.0 |

TABLE 6

Summary of Inotrope and Vasoactive Use (patients received at least one treatment)

| | NAV-1 (N = 59) | Control (N = 53) | Total (N = 112) |
|---|---|---|---|
| DOBUTAMINE | 8 (13.5) | 8 (15.1) | 16 (14.2) |
| DOPAMINE | 1 (1.7) | 2 (3.8) | 3 (2.7) |
| EPINEPHRINE | 12 (20.3) | 15 (28.3) | 27 (24.1) |
| GLYCERYL TRINITRATE | 49 (83.1) | 49 (92.5) | 98 (87.5) |
| NITROPRUSSIDE SODIUM | 16 (27.1) | 11 (20.8) | 27 (24.1) |
| NOREPINEPHRINE | 41 (69.5) | 34 (64.2) | 75 (67.0) |

CONCLUSIONS

This study was of an innovative critical care device for hemodynamic guidance. The study shows that 24 hour continuous beside circulation guidance is possible, effective and safe. It is surprising that a computer guidance system can adjust to the complex, often chaotic, circulatory dynamics in this critically-ill patient group. Using the a priori end-point of average standardized distance (ASD), the study showed that Navigator was the same or better than conventional care in achieving circulatory control to physician-set targets, with a mean benefit of a 10.9% reduction in ASD. The secondary endpoint of % time in target zone was also a same or better result with an increase from 32.4% in the control group to 38.4% in the Navigator group, a relative increase of 18.5%. Patients managed with Navigator were resuscitated more quickly. By the third hour after ICU admission, Navigator patients were in the target zone 44% of the time, compared with 30% in the control group (p=047). Navigator patients were maintained better at target levels. Over the subsequent 8 hours of care, Navigator patients were in target 40% of the time, and control patients 33% of the time. There was strong centre heterogeneity. When results were corrected post hoc for this heterogeneity, there was a strong trend towards superiority. Levels of ASD (Navigator 1.71, Control 1.92) were higher than that used in power calculations (1.30), which were based on data from the development centre. Thus the study may have been underpowered (though this was not detected at the interim analysis point). Data from NAV-1 will be very helpful in powering future studies. The average standardized distance (ASD) measure is similar to measures of average control error used in process engineering. However, it is unfamiliar to clinicians and hard to interpret. We have found that the percentage time in target zone is more intuitive and lends itself to clinical interpretation. Further it corresponds closely to the intended use of Navigator which is to help clinicians drive the circulation into the target zone. Cardiac surgery patients recovering in ICU are a well defined group for recruitment into clinical studies. They also present a wide range of unstable haemodynamic situations and range of therapeutic interventions. However, there are other patient groups, such as high-risk surgery and sepsis, where outcomes benefits have been demonstrated for goal-directed therapy (usually in oxygen delivery terms). These patient groups may be appropriate for future Navigator studies. It will be appreciated that numerous variations and/or modifications may be made to the embodiments disclosed without departing from the spirit or scope of the inventions as broadly described.

What is claimed is:

1. A computer-assisted method for providing therapeutic guidance of a subject's circulatory state, said method comprising the steps of:
   using a processing unit:
   (i) determining said subject's present and desired circulatory states as a function of at least mean systemic filling pressure ($P_{ms}$), heart efficiency ($E_H$) and systemic vascular resistance (SVR);
   (ii) determining a target direction of a trajectory from said subject's present circulatory state to said subject's desired circulatory state, wherein treatment of said subject so as to traverse said trajectory will cause said subject's circulatory state to move towards a desired circulatory state; and
   (iii) visually representing the target direction of said trajectory to assist in the treatment.

2. A computer-assisted method of claim 1, wherein the method provides a treatment sequencing guidance.

3. The computer-assisted method of claim 1, wherein said steps (i) to (iii) are performed repeatedly based on updated values of said subject's present and/or desired state.

4. The computer-assisted method of claim 1, wherein treatment of said subject so as to traverse said trajectory will cause said subject's mean arterial pressure (MAP) and cardiac output (CO) to converge to said subject's desired circulatory state.

5. The computer-assisted method of claim 1, wherein substantially continuous guidance is provided.

6. The computer-assisted method of claim 1, wherein intermittent guidance is provided.

7. The computer-assisted method of claim 1, wherein the method provides substantially continuous and/or intermittent guidance of said subjects circulatory state and/or control of hemodynamic and oxygen management of said subject's circulatory system.

8. The computer-assisted method of claim 1, wherein the method is used to provide substantially continuous and/or intermittent guidance of at least one of the following: fluid therapies for control of volume state, heart performance therapy, heart rate therapies, heart rhythm therapies and/or vasoactive therapies.

9. A computer program product comprising a computer readable medium comprising a computer program recorded therein for assessing a subject's circulation state, said computer program product comprising:
  (i) computer program code means for assisting in the determination of said subject's present circulatory state using at least mean systemic filling pressure ($P_{ms}$), heart efficiency ($E_H$) and systemic vascular resistance (SVR)
  (ii) computer program code means for assisting in the determination of said subject's desired circulatory state using at least mean systemic filling pressure ($P_{ms}$), heart efficiency ($E_H$) and systemic vascular resistance (SVR)
  (iii) computer program code means for visually representing said subject's present and desired circulatory states;
  (iv) computer program code means for determining a target direction of a trajectory from said subject's present circulatory state to said subject's desired circulatory state, wherein treatment of said subject so as to traverse said trajectory will cause said subject's mean arterial pressure (MAP) and cardiac output (CO) to converge to said subject's desired circulatory state; and
  (v) computer program code means for visually representing the target direction of said trajectory.

10. The computer program product of claim 9, further comprising computer program code means for executing said computer program code means (i) to (v) repeatedly based on updated values of said subject's present and/or desired state.

11. The computer program product of claim 9, wherein said computer program code means for determining a trajectory comprises:
  (vi) computer program code means for projecting MAP and CO isograms of said subject's present mean arterial pressure (MAP) and present cardiac output (CO) on said visual representation;
  (vii) computer program code means for bisecting an inner angle subtended by intersecting MAP and CO isograms, said inner angle in the quadrant the desired patient state is in; and
  (viii) computer program code means for selecting the bisection of said inner angle as the target direction of said trajectory.

12. The computer program product of claim 9, further comprising computer program code means for visually representing a target range for said subject's MAP and CO.

13. The computer program product of claim 9, further comprising computer program code means for controlling an infusion rate of a medication administered to said subject in accordance with said trajectory.

14. A circulatory monitoring and guidance system, comprising:
  a data acquisition unit;
  a visual display unit;
  a memory unit for storing data and instructions to be performed by a processing unit; and
  a processing unit coupled to said data acquisition unit, said visual display unit and said memory unit, said processing unit programmed to:
  (i) obtain subject specific parameters based on anthropometric data;
  (ii) acquire measured values of variables relating to said subject's circulation via said data acquisition unit;
  (iii) compute values of mean systemic filling pressure ($P_{ms}$), heart efficiency ($E_H$) and systemic vascular resistance (SVR) for said subject based on said subject specific parameters and said measured values;
  (iv) visually display said subject's present and desired circulatory states as a function of mean systemic filling pressure ($P_{ms}$), heart efficiency ($E_H$) and systemic vascular resistance (SVR) on said visual display unit;
  (v) determine a target direction of a trajectory from said subject's actual circulatory state to said subject's desired circulatory state, wherein treatment of said subject so as to traverse said trajectory will cause said subject's mean arterial pressure (MAP) and cardiac output (CO) to converge to said subject's desired circulatory state; and
  (vi) visually display the target direction of said trajectory on said visual display unit.

15. The circulatory monitoring and guidance system of claim 14, wherein said processing unit is programmed to execute steps (i) to (vi) repeatedly based on updated values of said subject specific parameters and said measured values.

16. The circulatory monitoring and guidance system of claim 14, wherein said processing unit is programmed to represent systemic vascular resistance (SVR) as an abscissa, mean systemic filling pressure ($P_{ms}$) as a primary ordinate and heart efficiency ($E_H$) as a secondary ordinate on said two-dimensional representation.

17. The circulatory monitoring and guidance system of claim 14, wherein said processing unit is programmed to control an infusion rate of a medication administered to said subject in accordance with said trajectory.

* * * * *